(12) United States Patent
Atterbury et al.

(10) Patent No.: US 11,925,790 B2
(45) Date of Patent: Mar. 12, 2024

(54) PROCESSES AND DEVICES FOR DELIVERY OF FLUID BY CHEMICAL REACTION

(71) Applicant: Eli Lilly and Company, Indianapolis, IN (US)

(72) Inventors: William Godwin Atterbury, Columbus, OH (US); Corrie Jo Bennison, Lewis Center, OH (US); Robert Jonathan Cain, Lewis Center, OH (US); Michael Funk Chiappetta, Greenwood, IN (US); Jeffrey Leclair Ellis, Columbus, OH (US); David Arthur Holley, Lancaster, OH (US); Mark Lafever, Indianapolis, IN (US); Beverly Ann Piatt, Columbus, OH (US); John Paul Tallarico, Powell, OH (US)

(73) Assignee: Eli Lilly and Company, Indianapolis, IN (US)

( * ) Notice: Subject to any disclaimer, the term of this patent is extended or adjusted under 35 U.S.C. 154(b) by 488 days.

(21) Appl. No.: 16/484,676

(22) PCT Filed: Feb. 9, 2018

(86) PCT No.: PCT/US2018/017547
§ 371 (c)(1),
(2) Date: Aug. 8, 2019

(87) PCT Pub. No.: WO2018/152018
PCT Pub. Date: Aug. 23, 2018

(65) Prior Publication Data
US 2020/0030537 A1    Jan. 30, 2020

Related U.S. Application Data

(60) Provisional application No. 62/460,414, filed on Feb. 17, 2017.

(51) Int. Cl.
*A61M 5/20* (2006.01)
*A61M 5/31* (2006.01)

(52) U.S. Cl.
CPC ... *A61M 5/2046* (2013.01); *A61M 2005/2073* (2013.01); *A61M 2005/3125* (2013.01);
(Continued)

(58) Field of Classification Search
CPC ........ A61M 5/2046; A61M 2005/2073; A61M 2005/3125; A61M 2205/7536;
(Continued)

(56) References Cited

U.S. PATENT DOCUMENTS 2,390,246 A  12/1945  Folkman
2,446,429 A   8/1948  Nelson et al.
(Continued)

FOREIGN PATENT DOCUMENTS

DE  3809482  10/1989
EP  2221076   8/2010
(Continued)

OTHER PUBLICATIONS

International Search Report of the International Searching Authority pertaining to International Application No. PCT/US2018/017547; dated Jul. 4, 2018; 8 pages.
(Continued)

*Primary Examiner* — Kami A Bosworth
(74) *Attorney, Agent, or Firm* — Jonathan C. Anderson

(57) ABSTRACT

Processes and devices provide parenteral delivery of therapeutic fluids, in particular high-viscosity therapeutic fluids (e.g., protein therapeutics), by a chemical reaction that generates a gas. A device may include a first actuation chamber containing a first reagent, a second reaction chamber containing a second reagent, and a third therapeutic fluid chamber containing the therapeutic fluid. In a loaded con-
(Continued)

figuration, a plunger separates the first chamber from the second chamber. In a delivery configuration, the plunger allows the first reagent from the first chamber to communicate and react with the second reagent from the second chamber. The generated gas acts upon a plunger to deliver the therapeutic fluid from the third chamber.

23 Claims, 24 Drawing Sheets

(52) U.S. Cl.
CPC .............. *A61M 2205/0216* (2013.01); *A61M 2205/7536* (2013.01)

(58) Field of Classification Search
CPC ........ A61M 5/2033; A61M 5/19; A61M 5/30; A61M 2205/8218; A61M 2205/8231; A61M 2005/14513; A61M 3/0237; A61M 3/0245; A61M 5/2448; A61M 2005/2451; A61M 5/284; A61M 5/3294; A61M 5/31596
See application file for complete search history.

(56) References Cited

U.S. PATENT DOCUMENTS

| | | | |
|---|---|---|---|
| 2,923,243 A | 2/1960 | Crockford et al. | |
| 3,405,845 A | 10/1968 | Cook et al. | |
| 3,467,526 A | 9/1969 | Mitchell et al. | |
| 3,594,410 A | 7/1971 | Cohen et al. | |
| 3,754,993 A | 8/1973 | Oguchi et al. | |
| 3,773,111 A | 11/1973 | Dunn | |
| 3,968,796 A | 7/1976 | Baker | |
| 4,031,889 A | 6/1977 | Pike | |
| 4,744,786 A | 5/1988 | Hooven | |
| 4,785,972 A | 11/1988 | LeFevre | |
| 4,795,748 A | 1/1989 | Ross et al. | |
| 5,034,114 A | 7/1991 | Kukin | |
| 5,062,834 A | 11/1991 | Gross et al. | |
| 5,151,093 A | 9/1992 | Theeuwes et al. | |
| 5,167,641 A | 12/1992 | Schmitz | |
| 5,304,128 A | 4/1994 | Haber et al. | |
| 5,312,389 A | 5/1994 | Theeuwes et al. | |
| 5,398,850 A | 3/1995 | Sancoff et al. | |
| 5,518,145 A | 5/1996 | Chen | |
| 5,540,665 A | 7/1996 | Mercado et al. | |
| 5,645,824 A | 7/1997 | Lim et al. | |
| 5,700,245 A | 12/1997 | Sancoff et al. | |
| 5,855,761 A | 1/1999 | Joshi | |
| 5,858,001 A | 1/1999 | Tsals et al. | |
| 5,871,125 A | 2/1999 | Gross | |
| 5,891,087 A | 4/1999 | Ohtani et al. | |
| 5,941,857 A | 8/1999 | Nguyen et al. | |
| 5,992,700 A | 11/1999 | McGlothlin et al. | |
| 6,086,568 A | 7/2000 | Caizza | |
| 6,086,569 A | 7/2000 | Schweizer | |
| 6,096,002 A * | 8/2000 | Landau ................... | A61M 5/30 604/143 |
| 6,156,014 A | 12/2000 | Petersen et al. | |
| 6,270,479 B1 | 8/2001 | Bergens et al. | |
| 6,431,468 B1 | 8/2002 | Brown et al. | |
| 6,575,961 B2 | 6/2003 | Joshi | |
| 6,830,560 B1 | 12/2004 | Gross et al. | |
| 6,913,593 B1 | 7/2005 | Alexandre et al. | |
| 6,964,356 B2 | 11/2005 | Kim | |
| 7,632,245 B1 | 12/2009 | Cowan et al. | |
| 7,717,877 B2 | 5/2010 | Lavi et al. | |
| 7,753,884 B2 | 7/2010 | Gallnböck | |
| 7,988,663 B2 | 8/2011 | Schiller et al. | |
| 8,157,769 B2 | 4/2012 | Cabiri | |
| 8,353,426 B2 | 1/2013 | Wold et al. | |
| 8,353,679 B2 | 1/2013 | Yamamoto et al. | |
| 9,321,581 B2 | 4/2016 | Bennison et al. | |
| 2001/0025168 A1 | 9/2001 | Gross et al. | |
| 2001/0050085 A1 | 12/2001 | Knudson et al. | |
| 2002/0156461 A1 | 10/2002 | Joshi | |
| 2003/0168480 A1 | 9/2003 | Kim | |
| 2004/0249339 A1 | 12/2004 | Willis et al. | |
| 2005/0006401 A1 | 1/2005 | Kim | |
| 2005/0063766 A1 | 3/2005 | Chen et al. | |
| 2005/0187522 A1 | 8/2005 | Miller | |
| 2006/0235264 A1 | 10/2006 | Vassallo | |
| 2007/0088337 A1 | 4/2007 | Lautenbach | |
| 2007/0228071 A1 | 10/2007 | Kamen et al. | |
| 2008/0066766 A1 | 3/2008 | Paraschac et al. | |
| 2008/0233029 A1 | 9/2008 | Fan et al. | |
| 2008/0257915 A1 | 10/2008 | Wold | |
| 2009/0093787 A1 | 4/2009 | Barbour | |
| 2009/0131860 A1 | 5/2009 | Nielsen | |
| 2009/0227942 A1 | 9/2009 | Stroem Hansen et al. | |
| 2009/0259176 A1 | 10/2009 | Yairi | |
| 2009/0259179 A1 | 10/2009 | Hillios et al. | |
| 2010/0030152 A1 | 2/2010 | Lee et al. | |
| 2010/0069846 A1 | 3/2010 | Stamp | |
| 2010/0137808 A1 | 6/2010 | Wilmot et al. | |
| 2010/0174225 A1 | 7/2010 | Pesach et al. | |
| 2011/0054390 A1 | 3/2011 | Searle et al. | |
| 2011/0092906 A1 | 4/2011 | Bottger et al. | |
| 2011/0270188 A1 | 11/2011 | Caffey et al. | |
| 2011/0272271 A1 | 11/2011 | Hong et al. | |
| 2012/0078216 A1 | 3/2012 | Smith et al. | |
| 2014/0103075 A1 | 4/2014 | Bennison et al. | |
| 2014/0330216 A1 | 11/2014 | Weaver et al. | |
| 2014/0364812 A1* | 12/2014 | Lumme ............... | A61M 5/3234 29/428 |
| 2015/0314070 A1 | 11/2015 | Heintz et al. | |
| 2016/0156060 A1 | 6/2016 | Hamelers et al. | |
| 2016/0213846 A1 | 7/2016 | Bennison et al. | |
| 2016/0213847 A1 | 7/2016 | Bennison et al. | |
| 2016/0213859 A1 | 7/2016 | Sadowski et al. | |
| 2017/0189609 A1* | 7/2017 | Wei .................... | A61M 5/14526 |
| 2019/0009026 A1* | 1/2019 | Gonzalez ............ | A61M 5/2033 |

FOREIGN PATENT DOCUMENTS

| | | | |
|---|---|---|---|
| EP | 2489387 | 8/2012 | |
| JP | H03178671 | 8/1991 | |
| WO | 92019571 | 11/1992 | |
| WO | 95001198 | 1/1995 | |
| WO | 95023641 | 9/1995 | |
| WO | 97028750 | 8/1997 | |
| WO | 99012593 | 3/1999 | |
| WO | 99022790 | 5/1999 | |
| WO | WO-9922790 A1 * | 5/1999 | .......... A61M 5/2046 |
| WO | 99062576 | 12/1999 | |
| WO | 01000270 | 1/2001 | |
| WO | 07071485 | 6/2007 | |
| WO | 09116045 | 9/2009 | |
| WO | 09144726 | 12/2009 | |
| WO | 2011039212 | 4/2011 | |
| WO | 2011075099 | 6/2011 | |
| WO | 2012122643 | 9/2012 | |
| WO | 14059444 | 4/2014 | |
| WO | 2015160600 | 10/2015 | |

OTHER PUBLICATIONS

Written Opinion of the International Searching Authority pertaining to International Application No. PCT/US2018/017547; dated Jul. 4, 2018; 15 pages.
"Development of an On-Demand, Generic, Drug-Delivery System," Southern Research Institute, 2000 Ninth Avenue South, Birmingham, AL 35255-5305 Aug. 6, 1985.
Good, Brian T., et al., "An Effervescent Reaction Micropump for Portable Microfluidic Systems," *Lab Chip*, 2006, 6, 659-66.

* cited by examiner

PROCESSES AND DEVICES FOR DELIVERY OF FLUID BY CHEMICAL REACTION

CROSS REFERENCE TO RELATED APPLICATION

This application is a National Stage of International Application No. PCT/US2018/017547, filed Feb. 9, 2018, which claims priority to U.S. Provisional Patent Application Ser. No. 62/460,414, filed Feb. 17, 2017, the disclosures of which are hereby expressly incorporated by reference herein in their entirety.

FIELD OF THE DISCLOSURE

The present disclosure relates to processes and devices for parenteral delivery of therapeutic fluids. More particularly, the present disclosure relates to processes and devices for parenteral delivery of high-viscosity therapeutic fluids (e.g., protein therapeutics) by a chemical reaction that generates a gas.

BACKGROUND OF THE DISCLOSURE

Protein therapeutics is an emerging class of drug therapy that provides treatment for a broad range of diseases, such as autoimmune disorders, cardiovascular diseases, diabetes, and cancer. A common delivery method for some protein therapeutics, such as monoclonal antibodies, is through intravenous infusion, in which large volumes of dilute solutions are delivered over time. Intravenous infusion usually requires the supervision of a doctor or nurse and is performed in a clinical setting. This can be inconvenient for a patient, and so efforts are being made to permit the delivery of protein therapeutics at home. Desirably, a protein therapeutic formulation can be administered using a syringe for subcutaneous delivery instead of requiring intravenous administration. Subcutaneous injections are commonly administered by laypersons, for example in the administration of insulin by diabetics.

Transitioning therapeutic protein formulations from intravenous delivery to injection devices like syringes and injection pens requires addressing challenges associated with delivering high concentrations of high molecular weight molecules in a manner that is easy, reliable, and causes minimal pain to the patient. In this regard, while intravenous bags typically have a volume of 1 liter, the standard volume for a syringe ranges from 0.3 milliliters up to 25 milliliters. Thus, depending on the drug, to deliver the same amount of therapeutic proteins, the concentration may have to increase by a factor of 40 or more. Also, injection therapy is moving towards smaller needle diameters and faster delivery times for purposes of patient comfort and compliance.

Delivery of protein therapeutics is also challenging because of the high viscosity associated with such therapeutic formulations, and the high forces needed to push such formulations through a parenteral device. Formulations with absolute viscosities above 40-60 centipoise (cP) may be difficult to deliver by conventional spring driven auto-injectors for multiple reasons. Structurally, the footprint of a spring for the amount of pressure or force delivered is relatively large and fixed to specific shapes, which reduces flexibility of design for delivery devices. Next, auto-injectors are usually made of plastic parts. However, a large amount of energy must be stored in the spring to reliably deliver high-viscosity fluids. If not properly designed, this stored energy may cause damage to the plastic parts due to creep, which is the tendency of the plastic part to permanently deform under stress. An auto-injector typically operates by using the spring to push a needle-containing internal component towards an outer edge of the housing of the syringe. The sound associated with the operation of a spring-based auto-injector may cause patient anxiety, potentially reducing future compliance. The generated pressure versus time profile of such a spring driven auto-injector cannot be readily modified, which prevents users from fine tuning pressure to meet their delivery needs.

It would be desirable to provide processes and devices by which a therapeutic fluid, in particular a high-viscosity fluid, could be self-administered in a reasonable time and with a limited injection space. These processes and devices could be used to deliver high-concentration protein, high-viscosity pharmaceutical formulations, or other therapeutic fluids.

SUMMARY

The present disclosure provides processes and devices for parenteral delivery of therapeutic fluids, in particular high-viscosity therapeutic fluids (e.g., protein therapeutics), by a chemical reaction that generates a gas. The device may include a first actuation chamber containing a first reagent, a second reaction chamber containing a second reagent, and a third therapeutic fluid chamber containing the therapeutic fluid. In a loaded configuration, a plunger separates the first chamber from the second chamber. In a delivery configuration, the plunger allows the first reagent from the first chamber to communicate and react with the second reagent from the second chamber. The generated gas acts upon a plunger to deliver the therapeutic fluid from the third chamber.

According to an embodiment of the present disclosure, a device is disclosed for delivering a therapeutic fluid by chemical reaction. The device includes a barrel having a first chamber, a second chamber, and a third chamber, a piston positioned between the first and second chambers of the barrel, a spring configured to move the piston, a plunger positioned between the second and third chambers of the barrel, and an actuator. The actuator has a locked configuration in which the actuator is prevented from moving axially relative to the barrel, an unlocked configuration in which the actuator is capable of moving axially relative to the barrel, and a delivery configuration in which the actuator moves axially relative to the barrel. In the locked and unlocked configurations, the first chamber contains a first reagent, the second chamber contains a second reagent and is separated from the first chamber by the piston, and the third chamber contains the therapeutic fluid. In the delivery configuration, the spring moves the piston to place the first chamber in communication with the second chamber, the first and second reagents reacting and generating a gas that drives the plunger to deliver the therapeutic fluid from the third chamber.

According to another embodiment of the present disclosure, a device is disclosed for delivering a therapeutic fluid by chemical reaction. The device includes a barrel having a first chamber, a second chamber, and a third chamber, a piston positioned between the first and second chambers of the barrel, a spring configured to move the piston, a plunger positioned between the second and third chambers of the barrel, and an actuator configured to rotate relative to the barrel between a first configuration and a second configuration. In the first configuration, the first chamber contains a first reagent, the second chamber contains a second reagent and is separated from the first chamber by the piston, and the third chamber contains the therapeutic fluid. In the second configuration, the spring moves the piston to place the first chamber in communication with the second chamber, the first and second reagents reacting and generating a gas that drives the plunger to deliver the therapeutic fluid from the third chamber.

According to yet another embodiment of the present disclosure, a device is disclosed for delivering a therapeutic fluid by chemical reaction. The device includes a barrel having a first chamber containing a first reagent, a second chamber containing a second reagent and an absorbent powder, and a third chamber containing the therapeutic fluid, a piston positioned between the first and second chambers of the barrel, a plunger positioned between the second and third chambers of the barrel, and an actuator configured to move the piston to place the first chamber in communication with the second chamber, the first and second reagents reacting and forming a liquid mixture and a gas, wherein at least a portion of the liquid mixture is absorbed by the absorbent powder, and wherein the gas drives the plunger to deliver the therapeutic fluid from the third chamber.

According to still yet another embodiment of the present disclosure, a device is disclosed for delivering a therapeutic fluid by chemical reaction. The device has a loaded configuration and a delivery configuration. The device includes a barrel, an actuator that moves in a first longitudinal direction relative to the barrel between the loaded configuration and the delivery configuration, a piston that moves in a second longitudinal direction opposite the first longitudinal direction of the actuator between the loaded configuration and the delivery configuration, and a locking mechanism that prevents movement of the actuator in the second longitudinal direction from the delivery configuration.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
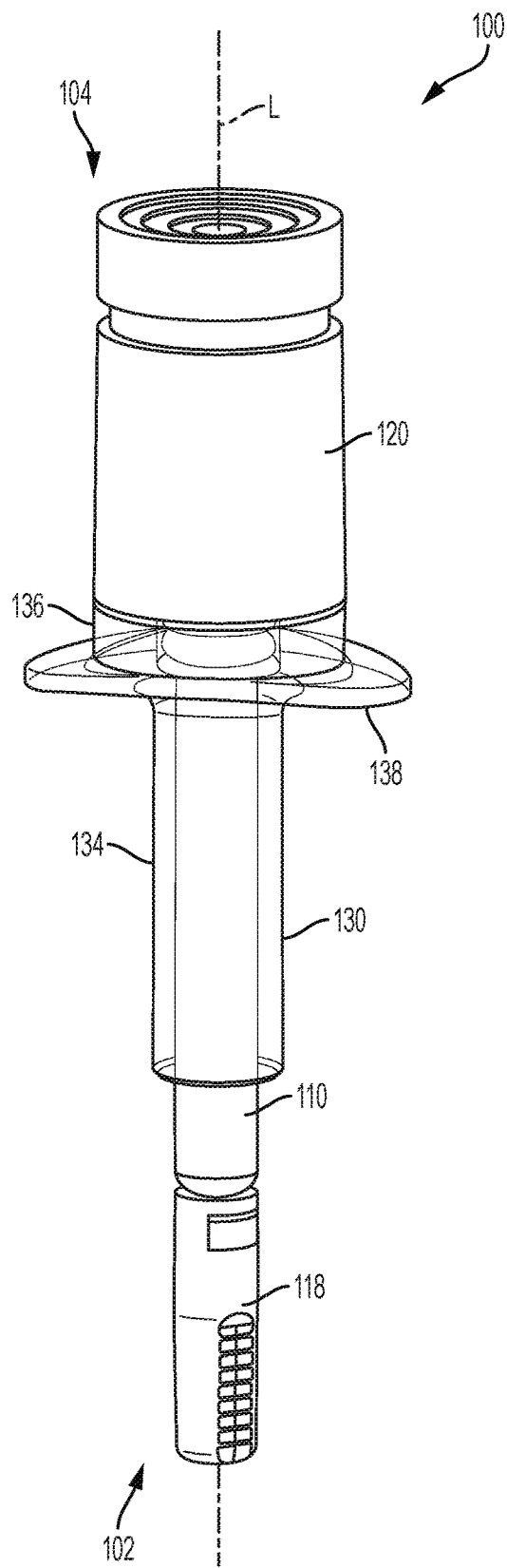
FIG. 1 is an assembled perspective view of a first exemplary delivery device of the present disclosure, the device including a syringe, an adapter, and an actuator assembly.

The present disclosure relates to processes and devices for parenteral delivery of high-viscosity therapeutic fluids. The device is driven by generating a gas in the device through a chemical reaction between one or more reagents. Suitable devices may include syringes or auto-injector pens, for example.

1. Therapeutic Fluids

The therapeutic fluid to be dispensed from the devices of the present disclosure may take various forms, such as a solution, dispersion, suspension, emulsion, or another suitable fluid form.

The therapeutic fluid may contain a therapeutically useful agent. In certain embodiments, the agent is protein, such as a monoclonal antibody or some other protein which is therapeutically useful. In some embodiments, the protein may have a concentration of from about 75 mg/mL to about 500 mg/mL in the therapeutic fluid. In certain embodiments, the protein may have a concentration of about 150 mg/mL, 200 mg/mL, 250 mg/mL, or more. The therapeutic fluid may further contain a solvent or non-solvent, such as water, perfluoroalkane solvent, safflower oil, or benzyl benzoate.

The therapeutic fluid may be considered a high-viscosity fluid and may have an absolute viscosity of from about 5 cP to about 1000 cP. In certain embodiments, the high-viscosity fluid has an absolute viscosity of at least about 10 cP, 20 cP, 30 cP, 40 cP, 50 cP, 60 cP, or more.

In some embodiments, the therapeutic fluid may include one or more drugs or therapeutic agents including but not limited to insulins, insulin analogs such as insulin lispro or insulin glargine, insulin derivatives, glucagon-like peptide (GLP-1) receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the device of the present disclosure. The drug as used in the device may be formulated with one or more excipients. The device is operated in a manner generally as described herein by a patient, caregiver or healthcare professional to deliver the drug to a person.

2. Gas-Generating Chemical Reactions

Any suitable chemical reagent or reagents can be used to generate a gas in the devices of the present disclosure. Examples of generated gases include carbon dioxide gas, nitrogen gas, oxygen gas, chlorine gas, etc. Desirably, the generated gas is inert and non-flammable. The amount of gas needed to operate the device may impact the type, amount, and concentration of each reagent used in the device. The reagents may be in dry form (e.g., powdered form, tablet form) and/or in liquid form.

In one exemplary embodiment, a bicarbonate (which may be present in dry form) reacts with an acid (which may be present in liquid form) to produce carbon dioxide gas in the device. Examples of suitable bicarbonates include sodium bicarbonate, potassium bicarbonate, and ammonium bicarbonate. Other ingredients may also be present along with the bicarbonates, such as diatomaceous earth. Examples of suitable acids include acetic acid, citric acid, potassium bitartrate, disodium pyrophosphate, and calcium dihydrogen phosphate. In one particular example, the bicarbonate is potassium bicarbonate and the acid is aqueous citric acid, which may react to produce carbon dioxide gas and a liquid mixture of water and dissolved potassium citrate.

Other reactions may be used to drive the devices of the present disclosure. In one example, a metal carbonate, such as copper carbonate or calcium carbonate, is thermally decomposed to produce carbon dioxide gas and the corresponding metal oxide in the device. In another example, 2,2'-azobisisobutyronitrile (AIBN) is heated to produce nitrogen gas in the device. In yet another example, enzymes (e.g. yeast) are reacted with sugar to produce carbon dioxide gas in the device. Some substances readily sublime, going from solid to gas. Such substances include but are not limited to naphthalene and iodine. In still yet another example, hydrogen peroxide is decomposed with catalysts such as enzymes (e.g. catalase) or manganese dioxide to produce oxygen gas in the device. In still yet another example, silver chloride is decomposed through exposure to light to generate a gas in the device. Suitable reagents, chemical formulations, and reactions used to drive the devices of the present disclosure are further described in U.S. application Ser. No. 14/434,586 (U.S. Publication No. 2015/0314070) titled "Chemical Engines and Methods for Their Use, Especially in the Injection of Highly Viscous Fluids," the disclosure of which is expressly incorporated herein by reference in its entirety.

3. First Delivery Device

Figure 2:
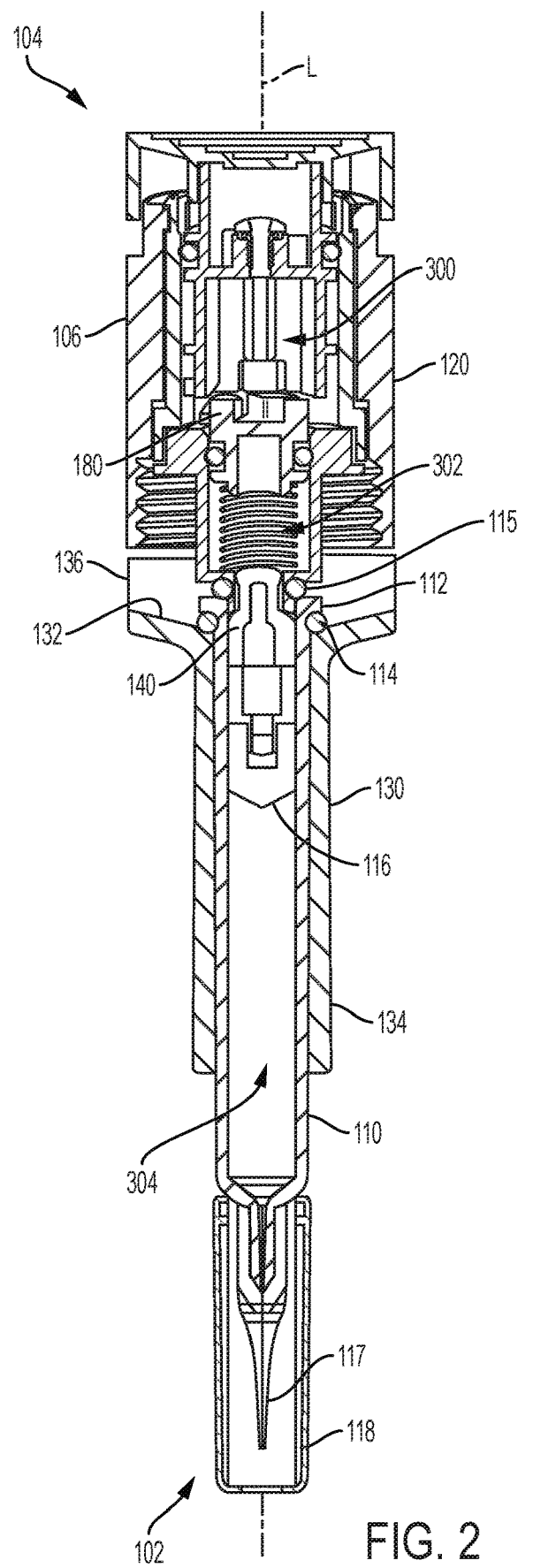
FIG. 2 is a cross-sectional view of the device of FIG. 1.
Figure 3:
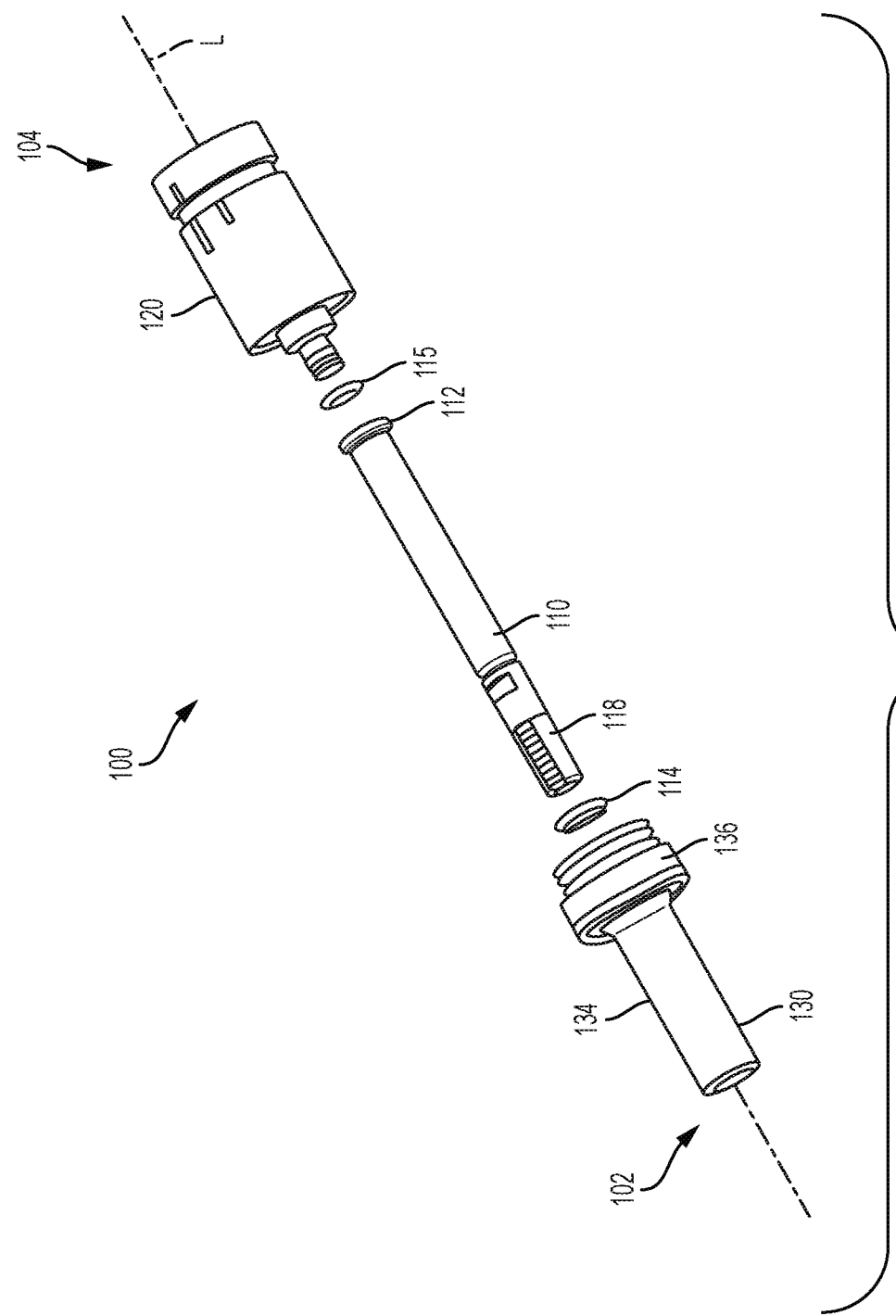
FIG. 3 is an exploded perspective view of the device of FIG. 1.

FIGS. 1-3 show a first exemplary delivery device 100 of the present disclosure. The illustrative device 100 is an elongate structure that extends along longitudinal axis L from a first, distal end 102 (illustratively, a lower end) to a second, proximal end 104 (illustratively, an upper end). The illustrative device 100 includes a substantially cylindrical barrel or housing 106 with a needle syringe 110 located at first end 102, an actuator assembly 120 located at second end 104, and a lower housing or adapter 130 located therebetween. These components are described further below. While actuator assembly 120 is illustratively coupled to syringe 110, actuator assembly 120 alternatively may be used with an auto-injector pen or other suitable delivery device.

Syringe 110 of device 100 may be constructed of glass, plastic, or another suitable material. As shown in FIGS. 2 and 3, the illustrative syringe 110 includes an upper rim 112 configured to rest upon an inner shoulder 132 of adapter 130. Beneath upper rim 112 of syringe 110, a damper 114 may be provided to dampen movement between syringe 110 and adapter 130. Damper 114 may be integrally coupled (e.g., overmolded) to syringe 110 and/or adapter 130. Alternatively, damper 114 may be a separate component (e.g., an O-ring). Above upper rim 112 of syringe 110, a seal 115 (e.g., an O-ring) may be provided to seal the connection between syringe 110 and actuator assembly 120. The illustrative syringe 110 also includes a plunger 116, a needle 117, and a protective end cap 118 over the needle 117.

Adapter 130 of device 100 includes a lower shaft 134 having a relatively small inner diameter and an upper head 136 having a relatively large inner diameter. Inner shoulder 132 is located between shaft 134 and head 136 of adapter 130 to receive rim 112 of syringe 110, as discussed above. Adapter 130 may be sized and shaped to receive a desired syringe 110. For example, the inner diameter of shaft 134 may be sized and shaped to accommodate the outer diameter of the desired syringe 110. When assembled, shaft 134 of adapter 130 extends downward to surround and support at least a portion of syringe 110, and head 136 extends upward to couple with actuator assembly 120. In the illustrated embodiment, head 136 of adapter 130 is externally threaded and actuator assembly 120 is internally threaded such that adapter 130 is threadably coupled with actuator assembly 120. It is also within the scope of the present disclosure to snap-fit, friction-fit, or otherwise couple adapter 130 to actuator assembly 120. Adapter 130 may also include a flange 138 (FIG. 1), illustratively an oval-shaped flange, that extends radially outward to serve as a gripping surface for the user.

Figure 4:
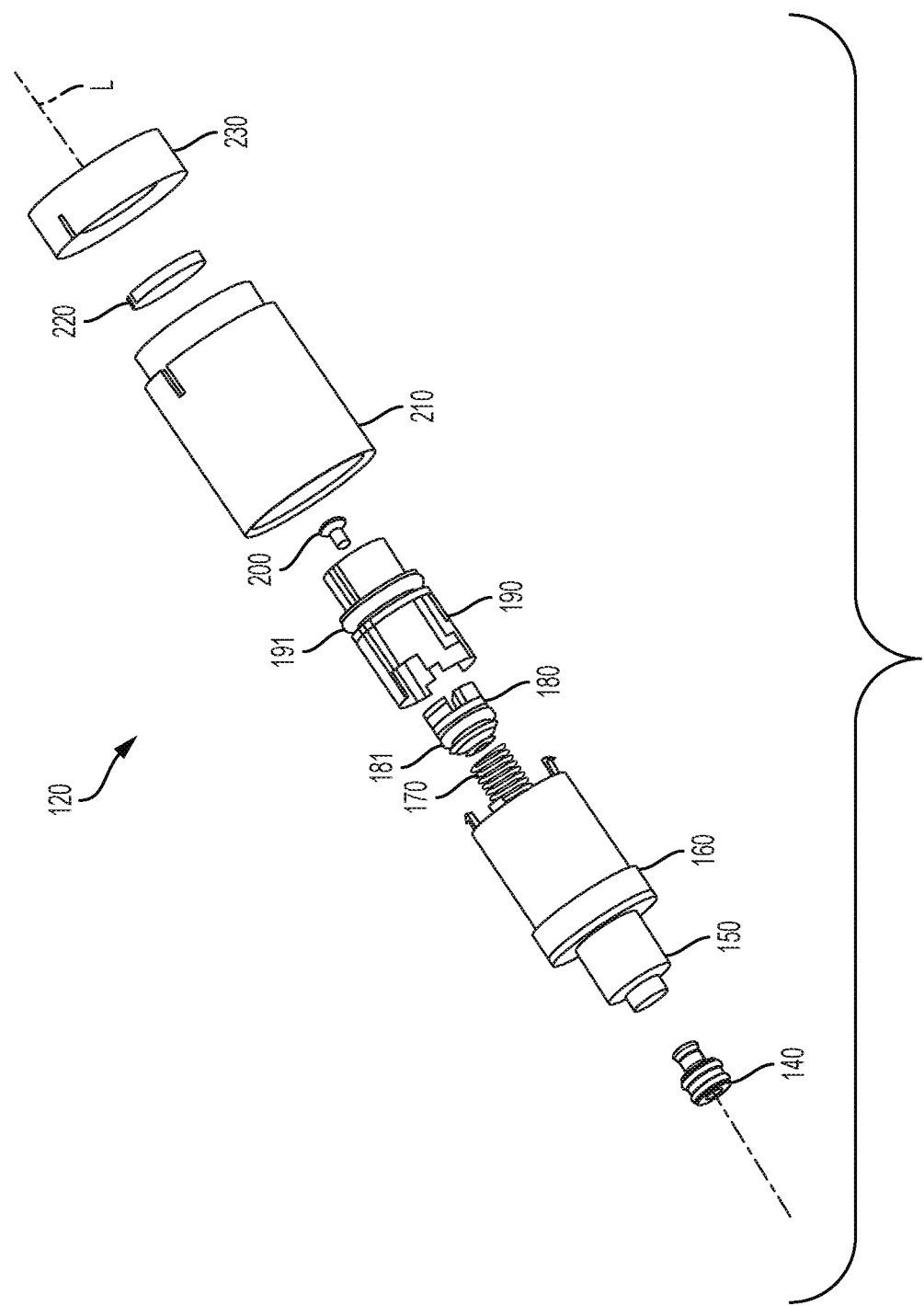
FIG. 4 is an exploded perspective view of the actuator assembly of FIG. 1, the actuator assembly including a lower plug, a lower mixing chamber, an upper mixing chamber, a helical spring, a piston, an actuator shuttle, an upper plug, an upper housing, an anti-back drive ring, and an actuator button.

Actuator assembly 120 of device 100 is shown in more detail in FIG. 4. The illustrative actuator assembly 120 includes the following components arranged along longitudinal axis L: a lower plug 140, a lower mixing chamber 150, an upper mixing chamber 160, a helical spring 170, a piston 180, an actuator shuttle 190, an upper plug or screw 200, an upper housing 210, an anti-back drive (ABD) ring 220, and an actuator button 230. Each of these components is described further below.

Figure 5:
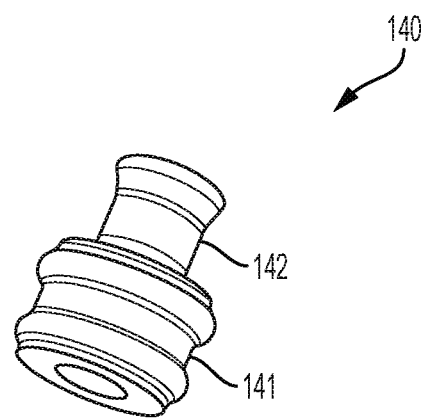
FIG. 5 is a perspective view of the lower plug of FIG. 4.
Figure 18:
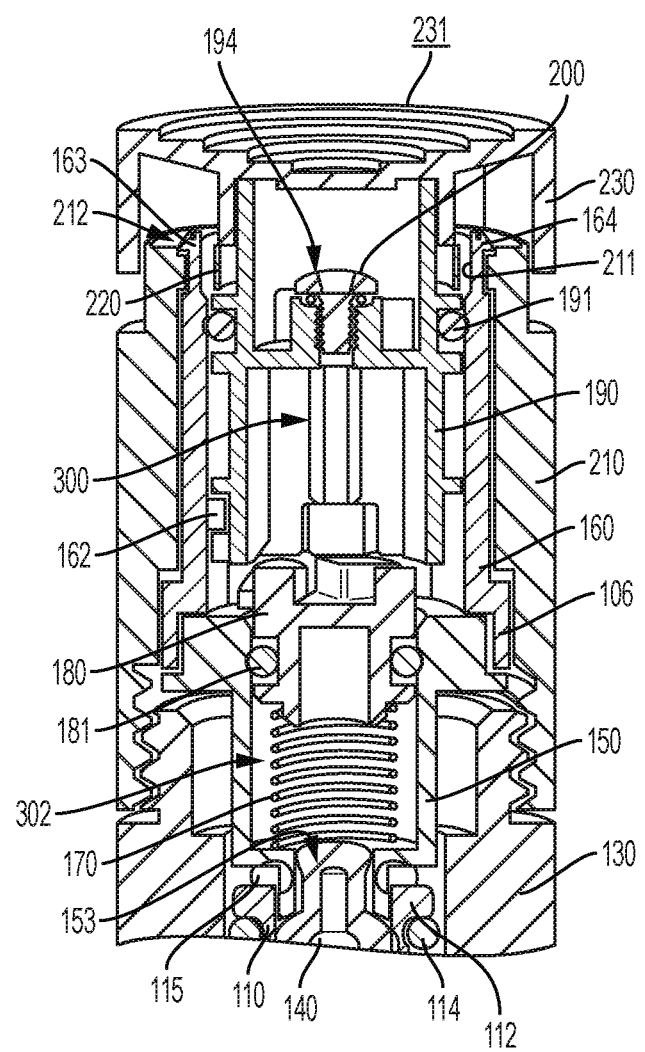
FIG. 18 is a cross-sectional view of the actuator assembly of FIG. 4 shown in a locked and loaded configuration.

Lower plug 140 is shown in FIG. 5. The illustrative plug 140 has a relatively large head 141 that is sized for receipt in syringe 110 and a relatively small shaft 142 that is sized for receipt in lower mixing chamber 150, as shown in FIG. 18. Lower plug 140 may be constructed of a thermoplastic elastomer (TPE) or another suitable material.

Figure 6:
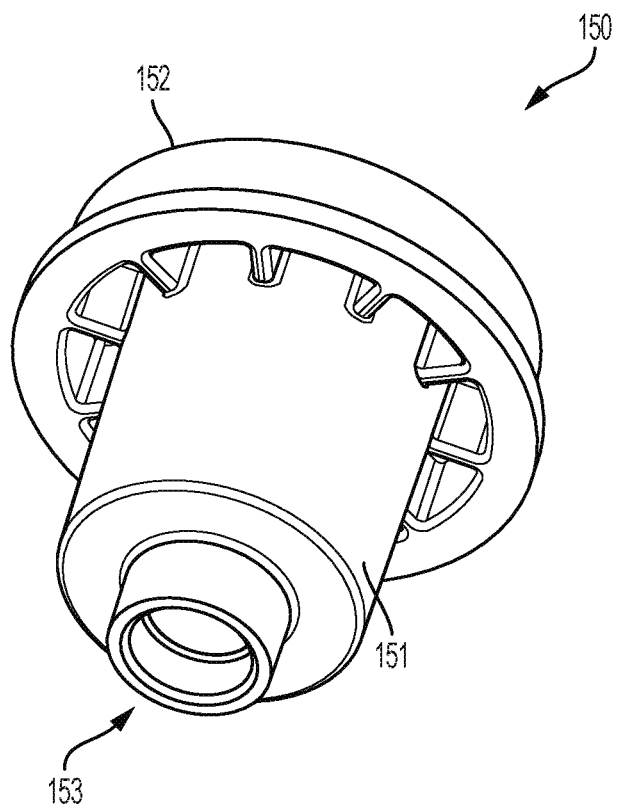
FIGS. 6 and 7 are perspective views of the lower mixing chamber of FIG. 4.
Figure 7:
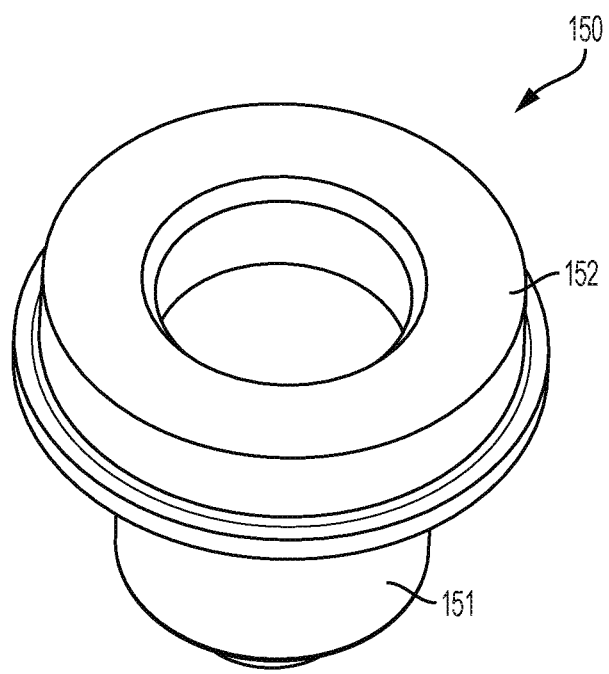

Lower mixing chamber 150 is shown in FIGS. 6 and 7. The illustrative lower mixing chamber 150 includes a lower portion 151 having a relatively small inner diameter and an upper portion 152 having a relatively large inner diameter. Lower portion 151 of lower mixing chamber 150 defines a lower port or hole 153 that is sized to receive lower plug 140, as shown in FIG. 18. Also, seal 115 is sized to fit around lower portion 151 of lower mixing chamber 150. Upper portion 152 of lower mixing chamber 150 is sized to receive spring 170 and piston 180, as shown in FIG. 18. Lower mixing chamber 150 may be constructed of a glass-reinforced high-density polyethylene (HDPE), glass-reinforced polypropylene, or another suitable material.

Figure 8:
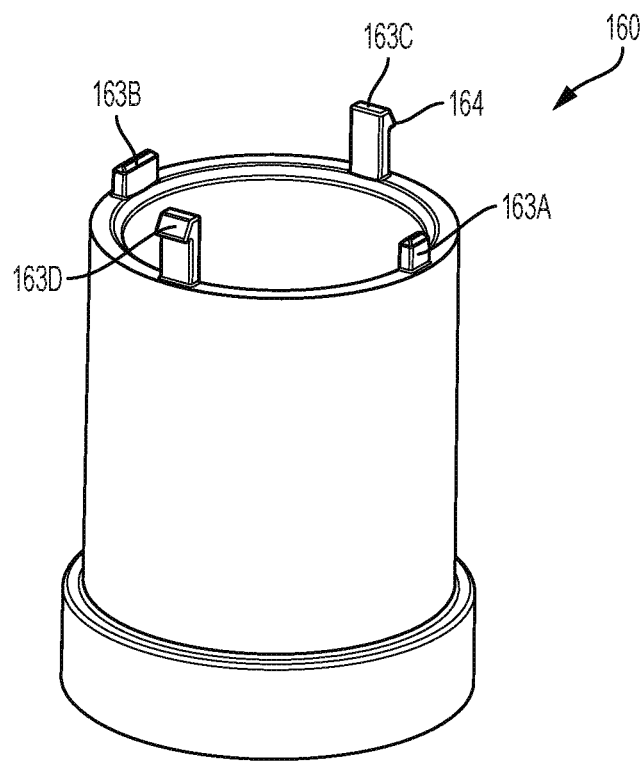
FIGS. 8 and 9 are perspective views of the upper mixing chamber of FIG. 4.
Figure 9:
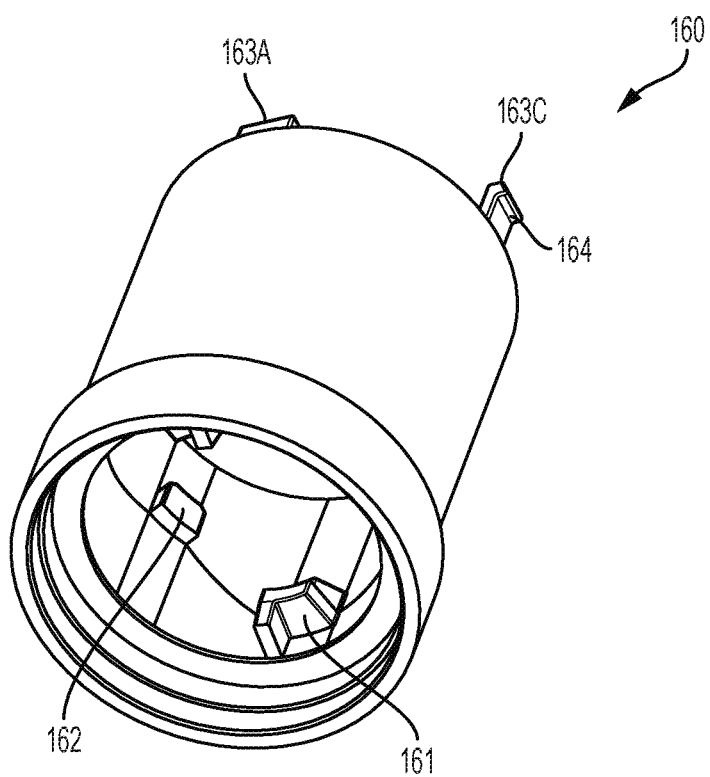

Upper mixing chamber 160 is shown in FIGS. 8 and 9. The illustrative upper mixing chamber 160 is coupled (e.g., ultrasonically welded) to lower mixing chamber 150, as shown in FIG. 18. It is also within the scope of the present disclosure that mixing chambers 150, 160 may be integrally formed together. Upper mixing chamber 160 has a larger inner diameter than lower mixing chamber 150 and is sized to receive shuttle 190, as shown in FIG. 18. Upper mixing chamber 160 includes one or more locking tabs 161 that extend radially inward to interact with piston 180 and one or more guide keys 162 that extend radially inward to interact with shuttle 190. More specifically, the illustrative upper mixing chamber 160 includes two locking tabs 161 positioned 180 degrees apart from one another and two guide keys 162 positioned 180 degrees apart from one another (see also FIG. 21). Locking tabs 161 may be relatively long radially to reach piston 180, whereas guide keys 162 may be relatively short radially to reach shuttle 190. Upper mixing chamber 160 also includes one or more alignment keys 163 that extend upward to interact with upper housing 210, illustratively a first alignment key 163A that is relatively wide, a second alignment key 163B that is relatively narrow, and third and fourth alignment keys 163C and 163D that are also relatively tall and narrow with coupling tabs 164 on their ends. Upper mixing chamber 160 may be constructed of a glass-reinforced HDPE, glass-reinforced polypropylene, or another suitable material.

Figure 10:
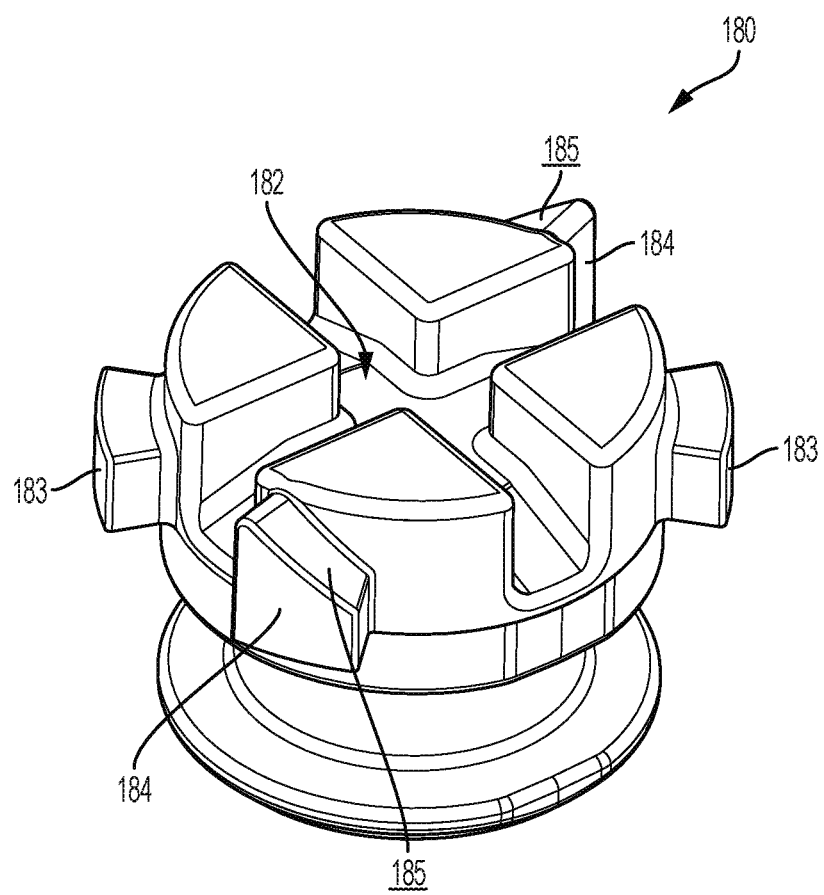
FIG. 10 is a perspective view of the piston of FIG. 4.

Piston 180 is shown in FIG. 10. The illustrative piston 180 is surrounded by a seal 181 (e.g., an O-ring), as shown in FIG. 18, to provide a sealing interface to the inner wall of lower mixing chamber 150. Piston 180 includes a tool engagement feature, illustratively crossed slots 182, that faces upward to interact with a rotation tool (not shown). Piston 180 also includes one or more locking tabs 183 that extend radially outward to interact with locking tabs 161 of upper mixing chamber 160 and one or more rotation tabs 184 that extend radially outward to interact with shuttle 190. More specifically, the illustrative piston 180 includes two locking tabs 183 positioned 180 degrees apart from one another and two rotation tabs 184 positioned 180 degrees apart from one another. Each rotation tab 184 has an upper ramped surface 185. Piston 180 may be constructed of a glass-reinforced HDPE, glass-reinforced polypropylene, or another suitable material.

Figure 11:
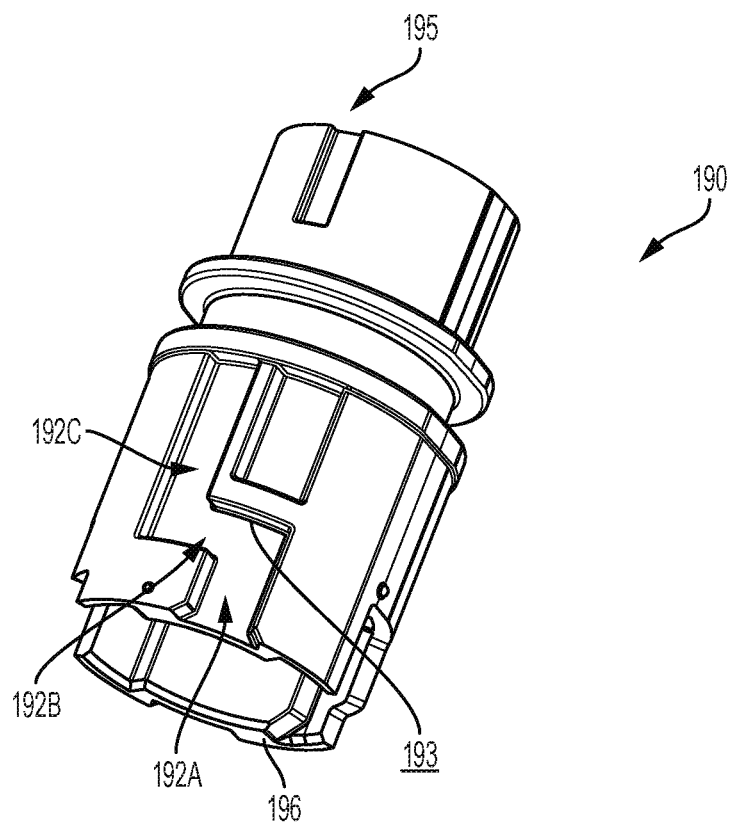
FIGS. 11 and 12 are perspective views of the shuttle of FIG. 4.
Figure 12:
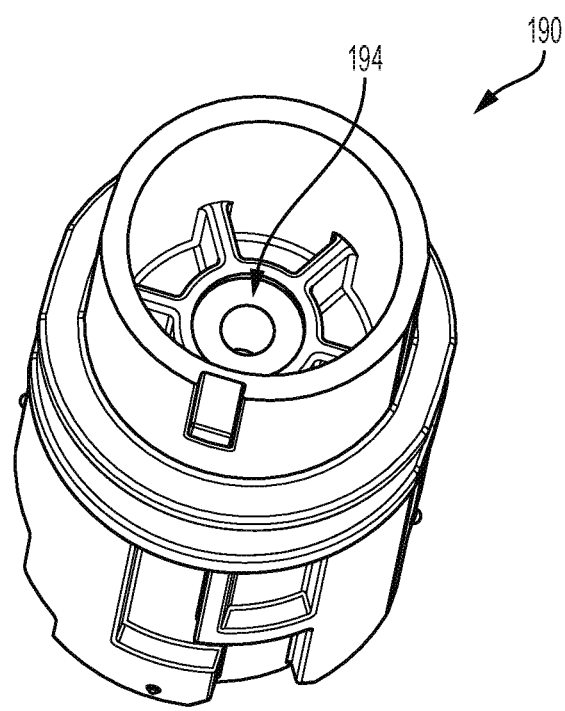

Shuttle 190 is shown in FIGS. 11 and 12. The illustrative shuttle 190 is surrounded by a seal 191 (e.g., an O-ring), as shown in FIG. 18, to provide a sealing interface to the inner wall of upper mixing chamber 160. Along its outer surface, shuttle 190 includes one or more step-shaped keyways 192, with each keyway 192 having a lower vertical portion 192A, an intermediate horizontal portion 192B, and an upper vertical portion 192C. The intermediate horizontal portion 192B of keyway 192 may be bordered by an upper wall or stop surface 193. At its upper end, shuttle 190 defines an upper port or hole 194 that is sized to receive upper plug 200 and an outer recess 195 that is configured to interact with button 230, as shown in FIG. 18. At its lower end, shuttle 190 includes one or more ramped surfaces 196 that are configured to interact with piston 180. Shuttle 190 may be constructed of a glass-reinforced HDPE, glass-reinforced polypropylene, or another suitable material.

Figure 13:
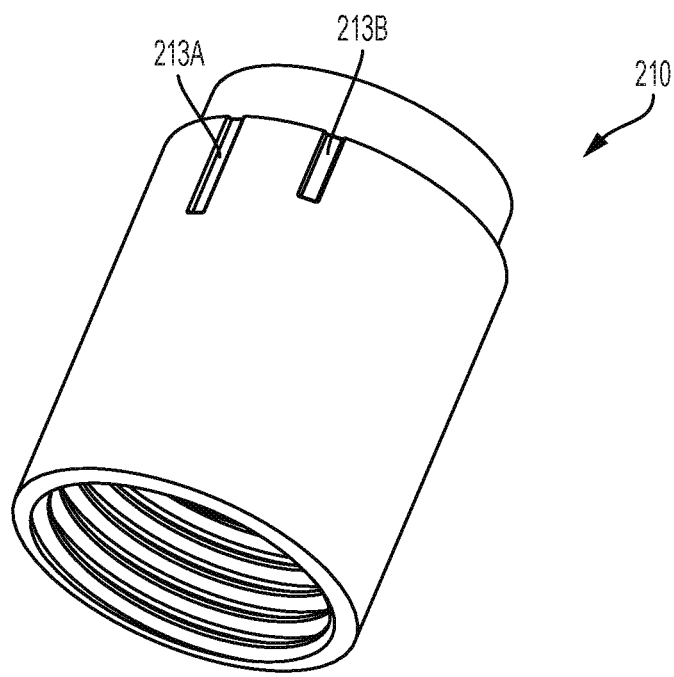
FIGS. 13 and 14 are perspective views of the upper housing of FIG. 4.
Figure 14:
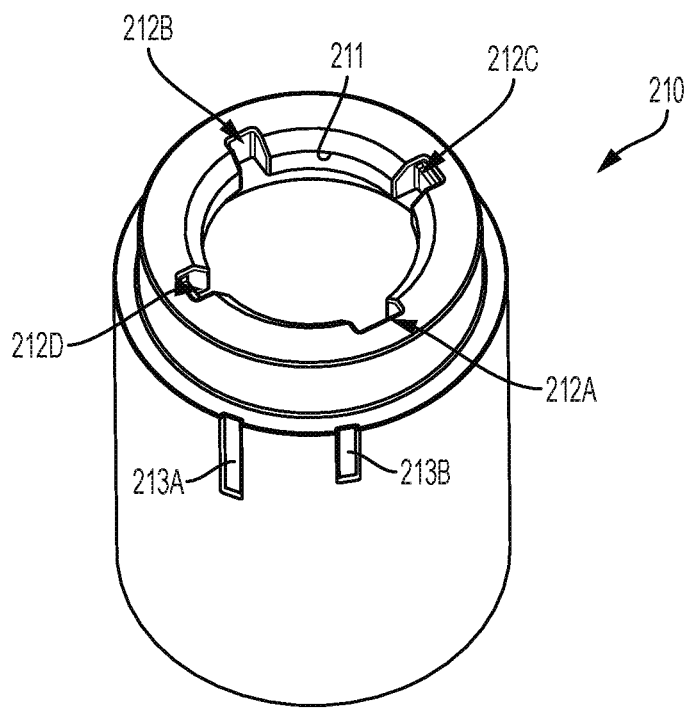

Upper housing 210 is shown in FIGS. 13 and 14. At its lower end, upper housing 210 is internally threaded to receive adapter 130, as shown in FIG. 18. At its upper end, upper housing 210 includes an inner rim 211 configured to interact with ABD ring 220, as shown in FIG. 18. Along its inner surface, upper housing 210 includes one or more alignment keyways 212 that are configured to receive corresponding alignment keys 163 of upper mixing chamber 160, illustratively a first alignment keyway 212A, a second alignment keyway 212B that is relatively narrow, and third and fourth alignment keyways 212C and 212D that are also relatively narrow. Along its outer surface, upper housing 210 includes locked indicator 213A and an unlocked indicator 213B. Upper housing 210 may be constructed of a glass-reinforced HDPE, acrylonitrile butadiene styrene (ABS), or another suitable material.

Figure 15:
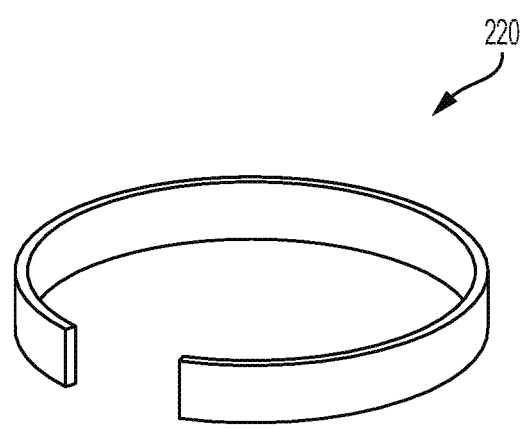
FIG. 15 is a perspective view of the anti-back drive ring of FIG. 4.

ABD ring 220 is shown in FIG. 15. The illustrative ABD ring 220 is a C-shaped spring that is biased radially outward to a relatively large diameter and configured to flex or compress radially inward to a relatively small diameter. ABD ring 220 may be constructed of stainless steel or another suitable material.

Figure 16:
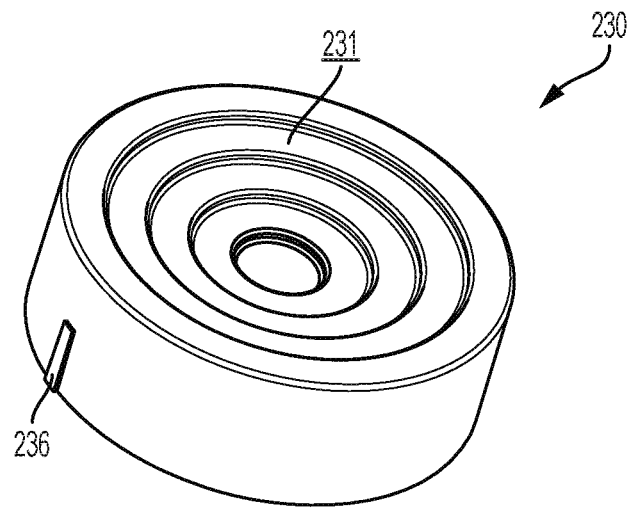
FIGS. 16 and 17 are perspective views of the button of FIG. 4.
Figure 17:
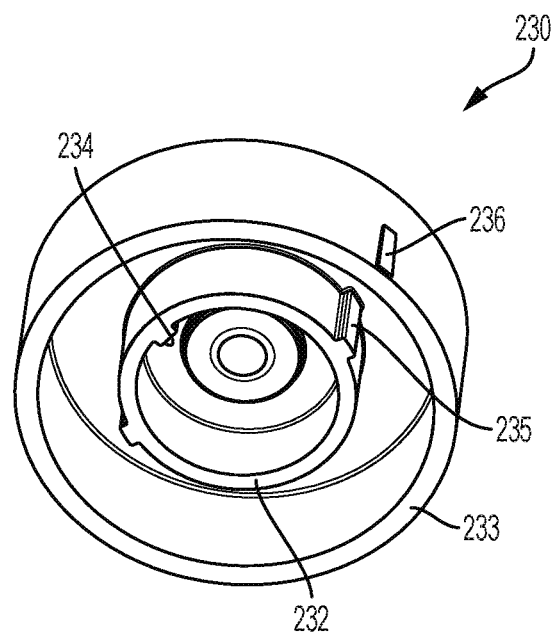

Button 230 is shown in FIGS. 16 and 17. The illustrative button 230 includes a contact surface 231, an inner ring 232, and an outer ring 233. The inner ring 232 includes one or more inner ribs 234 that extend radially inward to interact with recess 195 of shuttle 190 and one or more outer ribs 235 that extend radially outward above ABD ring 220, which is shown in FIG. 18. The outer ring 233 includes a lock indicator 236 configured to align selectively with locked indicator 213A or unlocked indicator 213B of upper housing 210, as shown in FIG. 4. Button 230 may be constructed of ABS, polycarbonate (PC), polyacrylate (PA), or another suitable material.

The illustrative actuator assembly 120 may be assembled with reference to FIG. 18 according to the following exemplary assembly process, although the order of these steps may vary. Once assembled, syringe 110, lower mixing chamber 150, upper mixing chamber 160, and upper housing 210 of device 100 may cooperate to define barrel 106 of device 100.

First, ABD ring 220 is installed in upper housing 210. This step may involve pressing ABD ring 220 downward until inner rim 211 of upper housing 210 compresses ABD ring 220 radially inward. The compressed ABD ring 220 will expand radially outward as far as possible to engage inner rim 211 of upper housing 210.

Second, spring 170 is installed in lower mixing chamber 150. This step may involve inserting spring 170 into upper mixing chamber 160 and allowing spring 170 to slide downward into lower mixing chamber 150.

Figure 21:
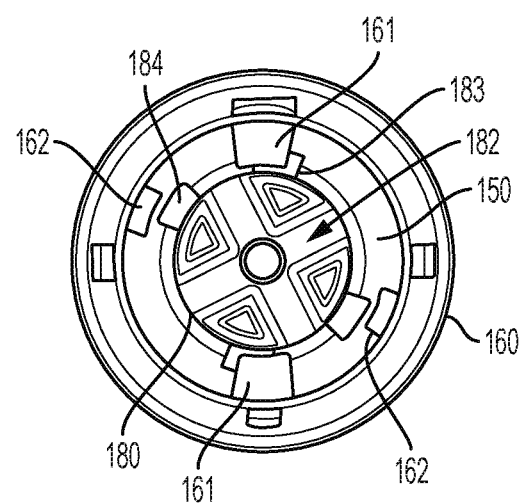
FIG. 21 is a top plan view of the mixing chambers and piston of FIG. 4 with the shuttle removed.

Third, piston 180 is installed in mixing chambers 150, 160. This step may involve forcing piston 180 downward to compress spring 170 and rotating piston 180 until locking tabs 183 on piston 180 are aligned beneath corresponding locking tabs 161 on upper mixing chamber 160, as shown in FIG. 21. A rotation tool (e.g., a screw driver) (not shown) may engage crossed slots 182 of piston 180 to depress and rotate piston 180. Piston 180 may be biased upward into engagement with internal locking tabs 161 of upper mixing chamber 160 under the force of the compressed spring 170. In this position, seal 181 on piston 180 may be sealed against lower mixing chamber 150.

Fourth, shuttle 190 is installed in upper mixing chamber 160 above piston 180. This step may involve moving shuttle 190 downward as guide key 162 of upper mixing chamber 160 travels through keyway 192 of shuttle 190. More specifically, guide key 162 travels through the lower vertical portion 192A of keyway 192 until reaching the intersection between the lower vertical portion 192A and the intermediate horizontal portion 192B of keyway 192, as shown with reference to FIG. 19. In this position, stop surface 193 may abut internal guide key 162 of upper mixing chamber 160 to prevent further downward movement of shuttle 190. Shuttle 190 may be biased upward relative to upper mixing chamber 160 under the force of the compressed spring 170.

Fifth, lower mixing chamber 150 is loaded with a second reagent (not shown). This step may involve inserting the second reagent through lower hole 153 in lower mixing chamber 150. In one example, the second reagent is a bicarbonate powder, such as potassium bicarbonate in diatomaceous earth powder. Other suitable reagents are described in Section 2 above. The illustrative lower mixing chamber 150 may be sized to hold about 200 mg, 250 mg, 300 mg, or more of the second reagent, although this amount may vary. This step may also involve closing lower hole 153 with lower plug 140 after loading lower mixing chamber 150 with the second reagent. Lower plug 140 may be friction-fit into lower hole 153 of lower mixing chamber 150.

Sixth, upper housing 210 is installed on upper mixing chamber 160. This step may involve aligning keyways 212 of upper housing 210 with corresponding alignment keys 163 of upper mixing chamber 160. More specifically, this step may involve aligning the relatively wide first alignment keyway 212A of upper housing 210 with the relatively wide first alignment key 163A of upper mixing chamber 160, the relatively narrow second alignment keyway 212B of upper housing 210 with the relatively narrow second alignment key 163B of upper mixing chamber 160, and third and fourth alignment keyways 212C and 212D of upper housing 210 with third and fourth alignment keys 163C and 163D of upper mixing chamber 160. When upper housing 210 is lowered into position, coupling tabs 164 on the third and fourth alignment keys 163C and 163D snap over upper housing 210 to hold upper housing 210 in place relative to upper mixing chamber 160.

Seventh, shuttle 190 is loaded with a first reagent (not shown). This step may involve inserting the first reagent through upper hole 194 in shuttle 190. In one example, the first reagent is an aqueous citric acid. Other suitable reagents are described in Section 2 above. The illustrative shuttle 190 may be sized to hold about 500 μL, 550 μL, 600 μL, or more of the first reagent, although this amount may vary. This step may also involve closing upper hole 194 with upper plug 200 after loading shuttle 190 with the first reagent, such as by threading upper plug 200 into upper hole 194.

Eighth, button 230 is installed on shuttle 190. This step may involve aligning inner rib 234 of button 230 with outer recess 195 of shuttle 190 to rotationally lock button 230 and shuttle 190 together. In this position, indicator 236 on button 230 may align with locked indicator 213A on upper housing 210, as shown in FIG. 3. Button 230 may help conceal upper hole 194 in shuttle 190 and upper plug 200. Button 230 may also be friction fit, ultrasonically welded, or otherwise coupled to shuttle 190 for rotation therewith.

Finally, syringe 110 may be coupled to actuator assembly 120 using adapter 130. This connection is described further above.

Initially, device 100 may be provided in a loaded and locked configuration in which piston 180 is held downward to compress spring 170, as shown in FIGS. 2 and 18. In this loaded and locked configuration, barrel 106 of device 100 may be divided into multiple chambers, illustratively a first actuation chamber 300, a second reaction chamber 302, and a third therapeutic fluid chamber 304. The first actuation chamber 300 is located in upper mixing chamber 160 and shuttle 190 above piston 180 and contains the first reagent (e.g., aqueous citric acid). The second reaction chamber 302 is located in lower mixing chamber 150 below piston 180 and contains the second reagent (e.g., potassium bicarbonate). The third therapeutic fluid chamber 304 is located in syringe 110 below plunger 116 and contains the therapeutic fluid. These three chambers 300, 302, and 304 are coaxial, and each is depicted as having a cylindrical shape. Device 100 may be stored in this loaded and locked configuration.

When device 100 is ready for use, device 100 may be moved from the locked configuration to an unlocked configuration. This step may involve rotating button 230 relative to upper housing 210. Indicator 236 on button 230 may move away from locked indicator 213A on upper housing 210, as shown in FIG. 3, and into alignment with unlocked indicator 213B on upper housing 210.

Figure 19:
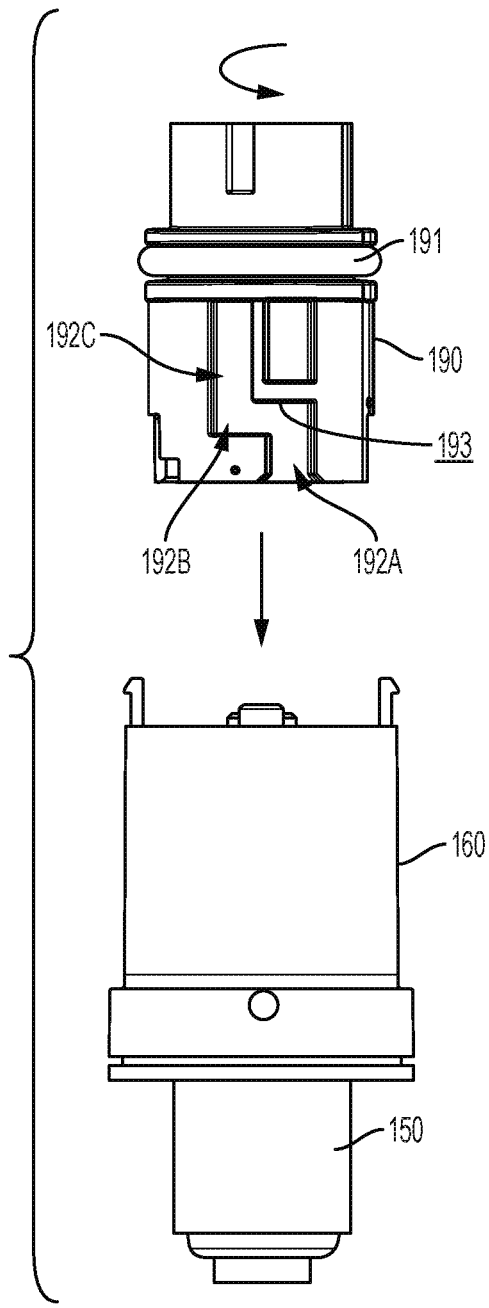
FIG. 19 is an exploded elevational view of the mixing chambers and the shuttle of FIG. 4.
Figure 20:
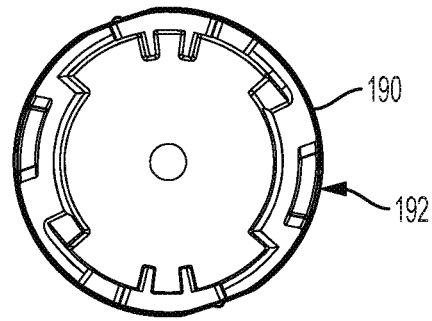
FIG. 20 is a bottom plan view of the shuttle of FIG. 4.

The rotation of button 230 causes rotation of shuttle 190, illustratively via the engagement between inner rib 234 on button 230 and outer recess 195 on shuttle 190. During this rotation, guide key 162 of upper mixing chamber 160 continues to travel through keyway 192 of shuttle 190, as shown in FIGS. 19-21. More specifically, guide key 162 travels through the intermediate horizontal portion 192B of keyway 192 until reaching the intersection between the intermediate horizontal portion 192B and the upper vertical portion 192C of keyway 192.

Figure 22:
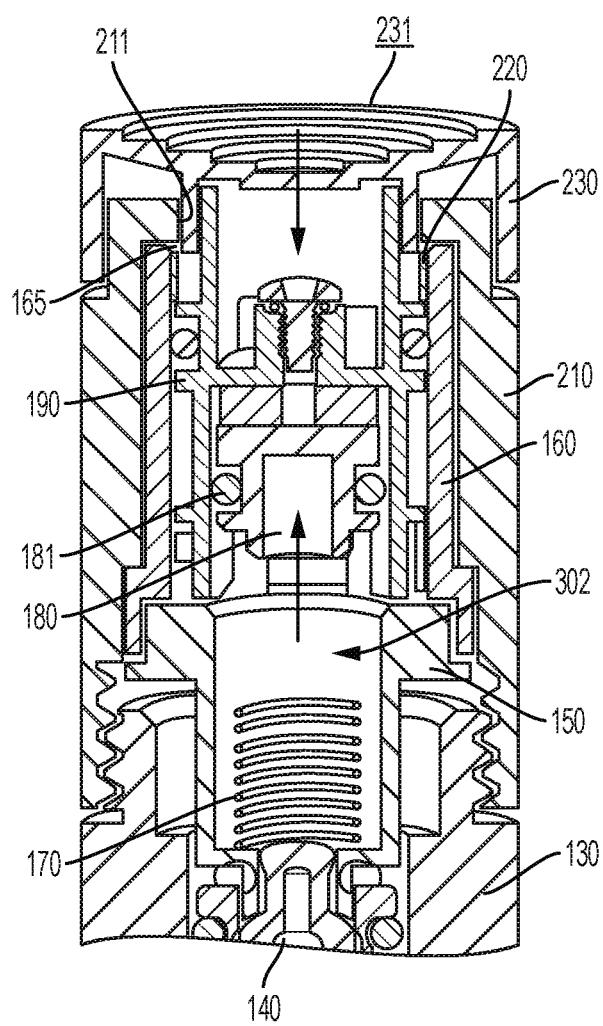
FIG. 22 is a cross-sectional view of the actuator assembly of FIG. 4 shown in a delivery configuration.

From the unlocked configuration, device 100 may be moved to an unloaded or delivery configuration to deliver the therapeutic fluid to a patient, as shown in FIG. 22. This step may involve pressing contact surface 231 of button 230 downward relative to upper housing 210.

The downward movement of button 230 causes downward movement of shuttle 190 relative to upper mixing chamber 160. Because button 230 and shuttle 190 operate together, the two components may be referred to collectively as an actuator. During this downward movement of shuttle 190, guide key 162 of upper mixing chamber 160 continues to travel through keyway 192 of shuttle 190, as shown in FIGS. 19-21. More specifically, guide key 162 travels through the upper vertical portion 192C of keyway 192.

Additionally, the downward movement of button 230, specifically outer ribs 235 of button 230, causes downward movement of ABD ring 220. When ABD ring 220 moves past inner rim 211 of upper housing 210, ABD ring 220 is free to expand radially outward into upper mixing chamber 160, as shown in FIG. 22. The expanded ABD ring 220 is captured beneath an upper lip 165 of upper mixing chamber 160. The expanded ABD ring 220 may serve as a locking mechanism by blocking upward movement of button 230 and shuttle 190 past upper lip 165 and holding button 230 and shuttle 190 downward in the delivery configuration, thereby preventing button 230 and shuttle 190 from returning upward to the initial, loaded configuration. Holding button 230 and shuttle 190 downward in the delivery configuration ensures that the volume inside barrel 106 remains consistent throughout the delivery process. Also, holding button 230 and shuttle 190 downward in the delivery configuration allows a user to visibly detect that device 100 has been used.

Figure 23:
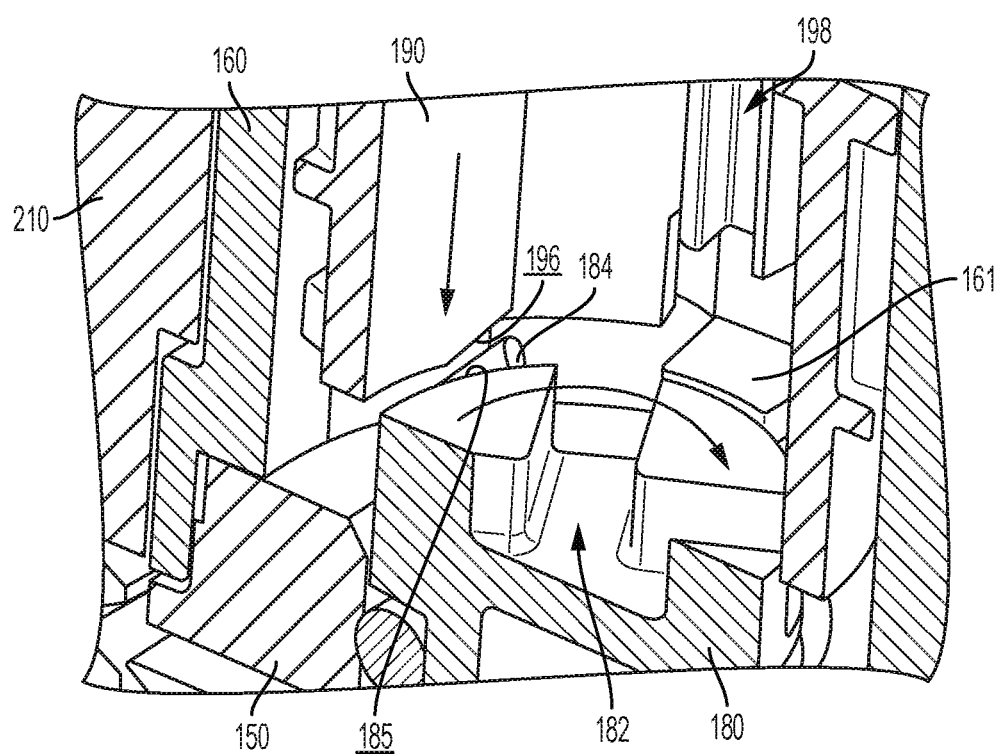
FIG. 23 is a vertical cross-sectional view of the actuator assembly moving toward the delivery configuration of FIG. 22.
Figure 24:
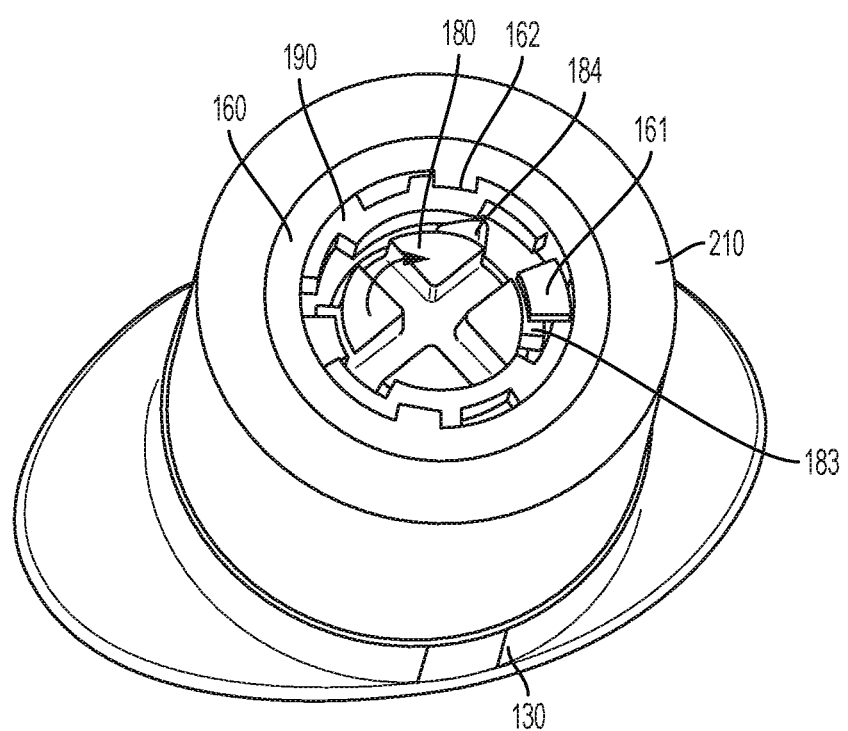
FIG. 24 is a horizontal cross-sectional view of the actuator assembly moving toward the delivery configuration of FIG. 22.

The downward movement of shuttle 190 causes rotation of piston 180. Ramped surfaces 196 of shuttle 190 engage corresponding ramped surfaces 185 of piston 180 to drive rotation of piston 180, as shown in FIG. 23. As piston 180 rotates, rotation tabs 184 of piston 180 are freed from beneath shuttle 190 and locking tabs 183 of piston 180 are freed from beneath locking tabs 161 of upper mixing chamber 160, as shown in FIG. 24.

The freed piston 180 moves upward and into shuttle 190 as spring 170 transitions from its compressed state to its neutral or released state, as shown in FIG. 22. During this transition, spring 170 should exert enough force to compress the air above piston 180 and to overcome the frictional forces between seal 181 and lower mixing chamber 150. The force exerted by spring 170 may be about 2.5 $lb_f$, 3.0 $lb_f$, 3.5 $lb_f$, 4.0 $lb_f$, 4.5 $lb_f$, or more, for example. In one particular example, spring 170 needs to exert about 2.0 $lb_f$ to compress the air above piston 180 and about 0.9 $lb_f$ to overcome frictional forces between seal 181 and lower mixing chamber 150, so spring 170 should be designed to exert at least about 2.9 $lb_f$, such as 3.6 $lb_f$.

The upward movement of piston 180 causes actuation chamber 300 to communicate with reaction chamber 302 by breaking the sealed interface therebetween. In the illustrated embodiment, shuttle 190 has a slightly larger inner diameter than lower mixing chamber 150, such that seal 181 on piston 180 seals against lower mixing chamber 150 in the loaded configuration of FIG. 18 but not against shuttle 190 in the delivery configuration of FIG. 22. Piston 180 may only need to travel a short distance before the sealed interface is broken, which allows for minimal head space above piston 180. The first reagent from actuation chamber 300 is exposed to the second reagent in reaction chamber 302, and this exposure leads to a gas-generating chemical reaction inside device 100. The space between seal 181 and shuttle 190 may be varied to control the speed at which the reagents are exposed to one another. For example, the inner surface of shuttle 190 may include one or more fluid delivery channels 198 (FIGS. 22 and 23) to encourage the first reagent to flow from actuation chamber 300, past piston 180, and into reaction chamber 302. One or more of the crossed slots 182 on piston 180 may rotate into alignment with fluid delivery channels 198 in the delivery configuration to further direct fluid flow across piston 180.

The generated gas causes the pressure in device 100 to increase. Because button 230 is retained downward in the delivery configuration and prevented from returning upward to the initial loaded configuration, the volume inside barrel 106 remains consistent throughout the delivery process and the pressure inside barrel 106 is forced to escape downward from device 100. Once a threshold pressure is reached inside device 100 and a corresponding threshold force is applied to lower plug 140, lower plug 140 may be forced downward from its pre-delivery or loaded position of FIG. 2 to a delivery position out of lower hole 153 and toward plunger 116. The downward movement of lower plug 140 pushes plunger 116 downward through syringe 110, and the downward movement of plunger 116 forces the therapeutic fluid out of therapeutic fluid chamber 304 through needle 117 for delivery to a patient. The threshold force on lower plug 140 may be about 0.1 $lb_f$, 0.2 $lb_f$, 0.3 $lb_f$, 0.4 $lb_f$, 0.5 $lb_f$, or more, for example. Device 100 may reach this threshold force quickly for rapid delivery of the therapeutic fluid to the patient. As the reaction continues, the pressure in device 100 may increase significantly beyond the threshold pressure. For example, the pressure in device 100 may reach about 200 psi, 300 psi, 400 psi, 500 psi, or more.

Device 100 may be configured to visibly indicate to a user when device 100 has been used in the delivery configuration. One example of this visible indication is the downward locking of button 230, as discussed above. Another example is the visible position of lower plug 140 and/or plunger 116 in device 100. In one embodiment, device 100 includes one or more windows (not shown) through which the user can see whether lower plug 140 and/or plunger 116 are in the pre-delivery or loaded position of FIG. 2 or the final delivery position. Labels (not shown) may be provided adjacent to the windows to further communicate the position of lower plug 140 and/or plunger 116 to the user. Yet another example is a visible pressure indicator inside reaction chamber 302. In one embodiment, device 100 includes one or more windows (not shown) through which the user can see a balloon (not shown) inside reaction chamber 302 that fills with the produced gas and expands during use.

In the exemplary embodiment, seals 115, 181, 191 are capable of withstanding the pressure and reactive conditions inside device 100. Exemplary materials for seals 115, 181, 191 include butyl rubber and fluoroelastomers (e.g., Viton® available from The Chemours Company).

Figure 25:
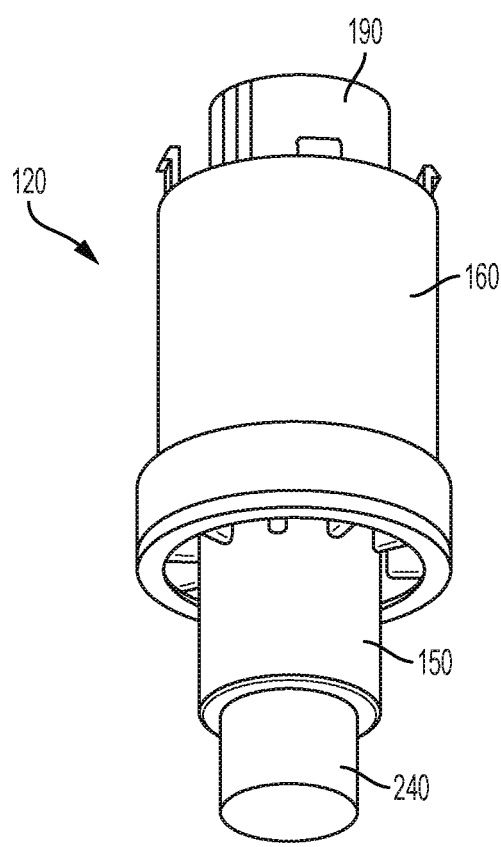
FIG. 25 is a perspective view of a modified actuator assembly including a lower cap.
Figure 26:
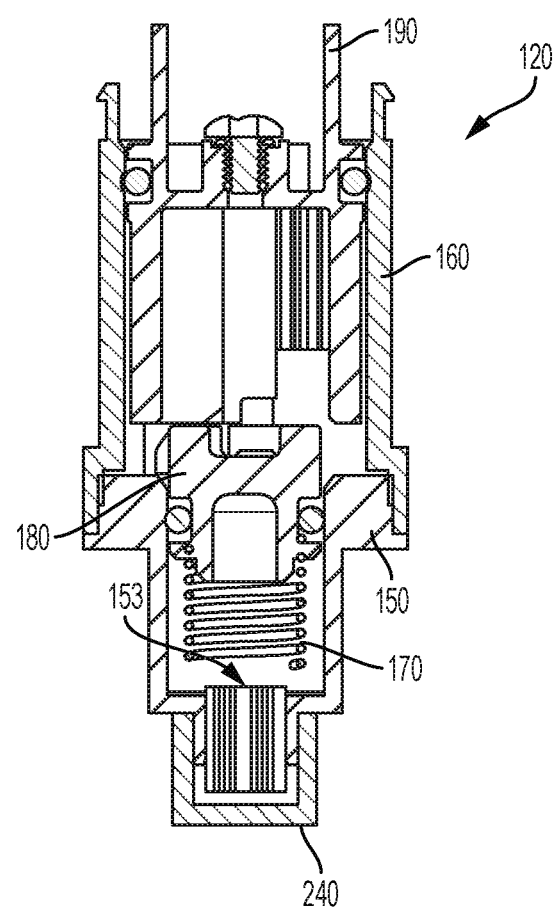
FIG. 26 is a cross-sectional view of the modified actuator assembly of FIG. 25.

FIGS. 25 and 26 show a modified version of actuator assembly 120 for use with device 100 (FIG. 2), in which the elastomeric lower plug 140 is replaced with a removable lower cap 240. Before actuator assembly 120 is coupled to syringe 110 (FIG. 2), lower cap 240 may be coupled to lower mixing chamber 150 to close lower hole 153 and retain the second reagent within lower mixing chamber 150. When actuator assembly 120 is ready to be coupled to syringe 110, lower cap 240 may be removed from lower mixing chamber 150. In one embodiment, a filter (e.g., filter 402 of FIG. 33) is positioned in lower hole 153 to help retain the reagent with lower cap 240 removed. Because the generated gas only has to move plunger 116 (FIG. 2), not lower plug 140, the modified device 100 may have lower pressure requirements.

4. Second Delivery Device

Figure 27:
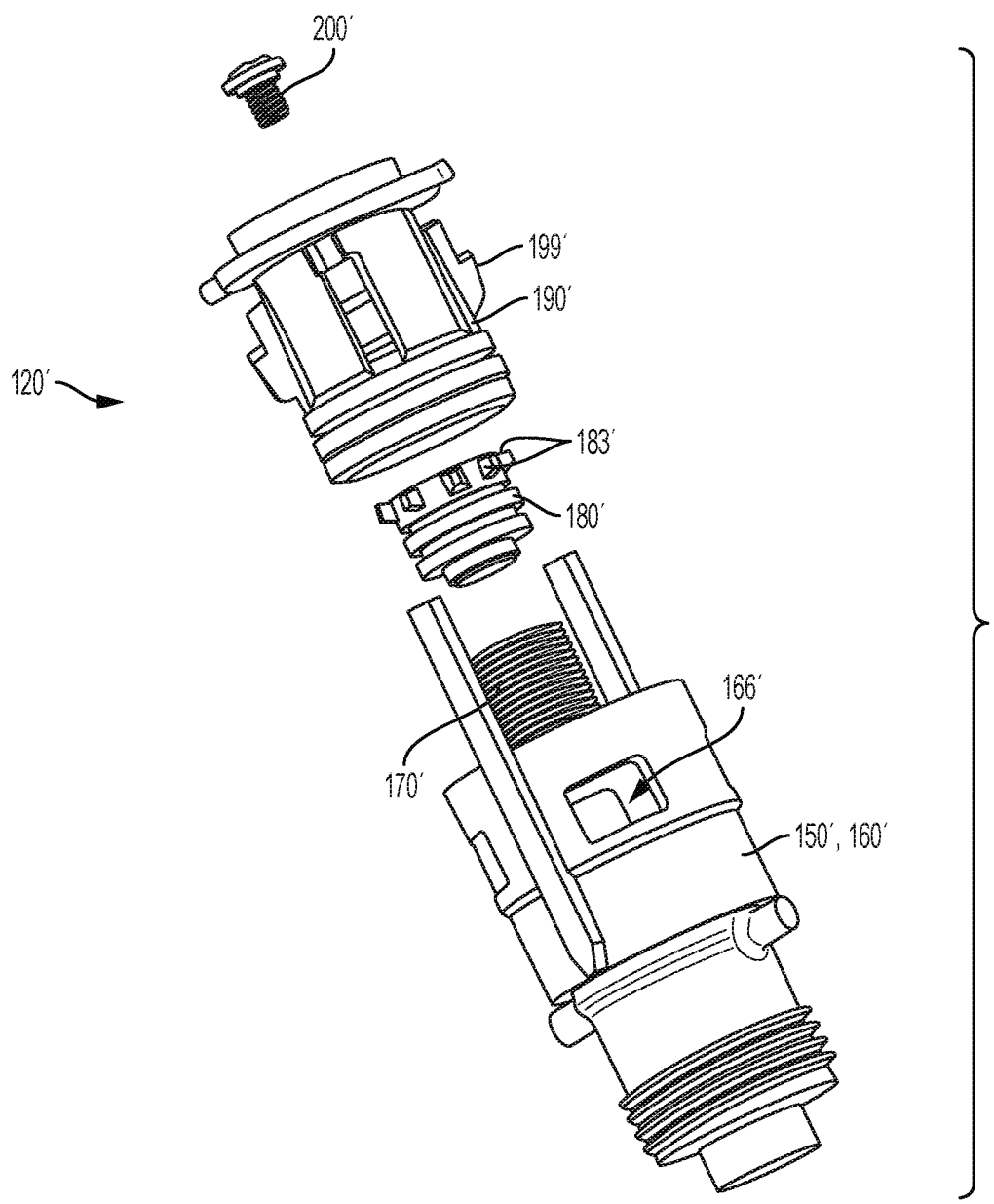
FIG. 27 is an exploded perspective view of a second exemplary actuator assembly of the present disclosure.

FIG. 27 shows an actuator assembly 120' of a second exemplary delivery device of the present disclosure. Actuator assembly 120' of the second exemplary delivery device is similar to actuator assembly 120 of device 100, with like reference numerals indicating like parts, except as described below. Like actuator assembly 120, actuator assembly 120' may be coupled to a syringe (e.g., syringe 110 of FIG. 2), an auto-injector pen, or another suitable delivery device. The following components of actuator assembly 120' are shown in FIG. 27: a lower mixing chamber 150', an upper mixing chamber 160', a helical spring 170', a piston 180', a shuttle 190', and an upper plug or screw 200'. Actuator assembly 120' may include additional components not shown in the drawings, such as a lower plug (similar to lower plug 140 of device 100), a lower cap (similar to lower cap 240 of device 100), and/or an actuator knob (similar to button 230).

The illustrative lower mixing chamber 150' and upper mixing chamber 160' are integrally formed together as a single unit. At its lower end, mixing chamber 150', 160' is externally threaded for coupling to an adapter (similar to adapter 130 of device 100). At its upper end, mixing chamber 150', 160' defines one or more lock indicator windows 166'. Mixing chamber 150', 160' is sized to receive spring 170', piston 180', and shuttle 190' in a stacked arrangement.

The illustrative piston 180' includes one or more locking tabs 183' that extend radially outward to interact with shuttle 190'. More specifically, the illustrative piston 180' includes eight locking tabs 183' positioned 45 degrees apart from one another around the circumference of piston 180'.

Figure 29:
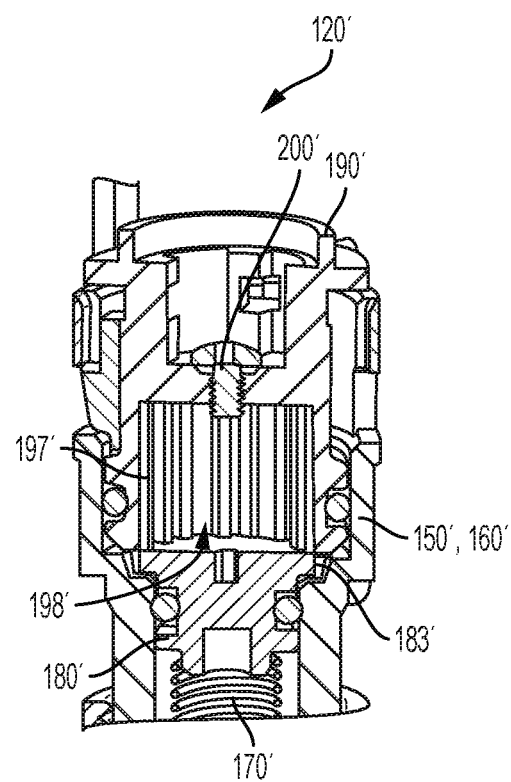
FIG. 29 is a cross-sectional view of the second actuator assembly of FIG. 28.

The illustrative shuttle 190' includes one or more locking tabs 197' that extend radially inward to interact with piston 180', as shown in FIG. 29. More specifically, the illustrative shuttle 190' includes eight locking tabs 197' positioned 45 degrees apart from one another around the circumference of shuttle 190'. Shuttle 190' also includes channels 198' between adjacent locking tabs 197'. At its upper end, shuttle 190' includes one or more dual-purposed lock indicator tabs 199' that both control and communicate the position of shuttle 190' relative to mixing chambers 150', 160'.

The illustrative actuator assembly 120' may be assembled by installing spring 170', piston 180' and shuttle 190' in mixing chambers 150', 160'. As shuttle 190' moves downward relative to mixing chambers 150', 160', lock indicator tab 199' flexes inward and then snaps outward into lock indicator window 166' to retain shuttle 190' in mixing chambers 150', 160'.

Figure 28:
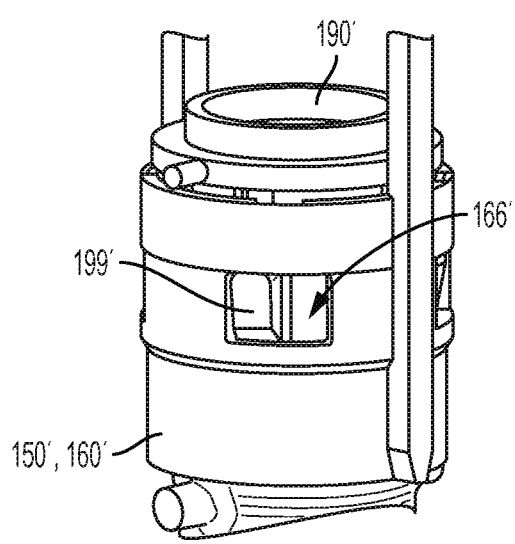
FIG. 28 is an assembled perspective view of the second actuator assembly of FIG. 27 shown in a locked and loaded configuration.

The assembled actuator assembly 120' may have a loaded and locked configuration in which piston 180' is held downward to compress spring 170', as shown in FIGS. 28 and 29. Piston 180' may be held in this position by aligning locking tabs 183' of piston 180' beneath locking tabs 197' of shuttle 190'. Lock indicator tab 199' of shuttle 190' is visible in a locked position (e.g., a leftward position) through the lock indicator window 166' of mixing chambers 150', 160'.

Figure 30:
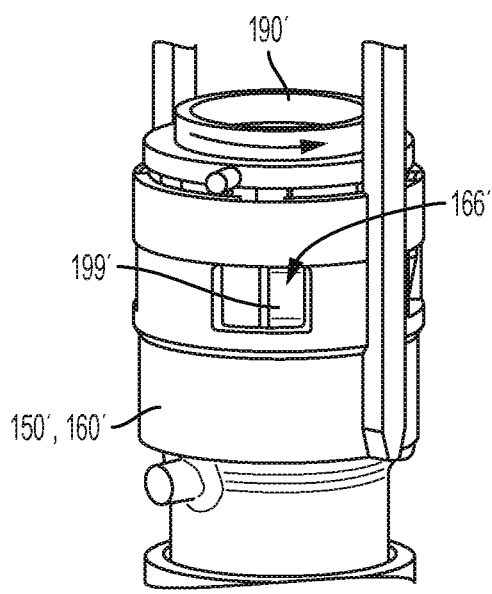
FIG. 30 is an assembled perspective view of the second actuator assembly of FIG. 27 shown in a delivery configuration.
Figure 31:
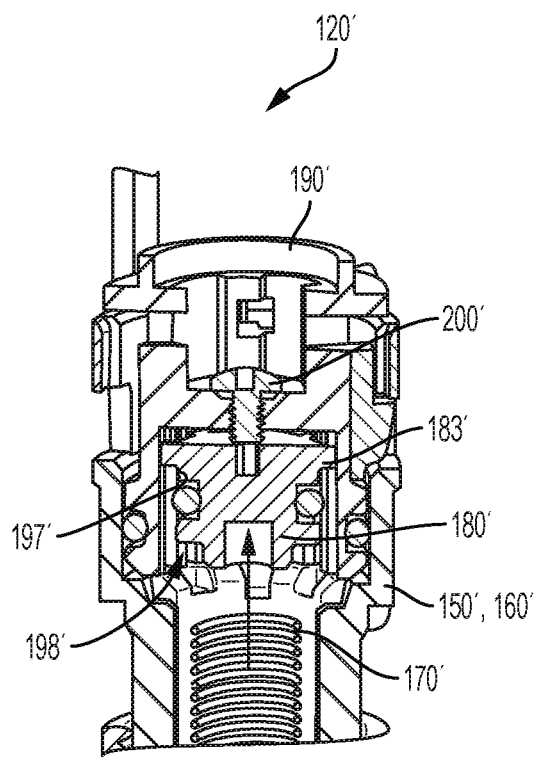
FIG. 31 is a cross-sectional view of the second actuator assembly of FIG. 30.

From the locked configuration, actuator assembly 120' may be moved to a delivery configuration, as shown in FIGS. 30 and 31. This step may involve rotating shuttle 190' relative to mixing chambers 150', 160' until locking tabs 197' of shuttle 190' are offset from locking tabs 183' of piston 180' and channels 198' of shuttle 190' are aligned with locking tabs 183' of piston 180'. Depending on the size and position of locking tabs 183', 197', the required rotation of shuttle 190' may be small, such as about 25 degrees, 20 degrees, 15 degrees, 10 degrees, or less. During this rotation, lock indicator tab 199' of shuttle 190' moves to an unlocked position (e.g., a rightward position) in the lock indicator window 166' of mixing chambers 150', 160'.

The freed piston 180' moves upward into shuttle 190' as spring 170' transitions from its compressed state to its neutral or released state. More specifically, locking tabs 183' of piston 180' move upward through channels 198' of shuttle 190'. The upward movement of piston 180' breaks the sealed interface on either side of piston 180' and allows fluid communication across piston 180'. Channels 198' of shuttle 190' may serve a dual-purpose in this embodiment. In addition to guiding locking tabs 183' of piston 180' upward, channels 198' of shuttle 190' may guide fluid flowing downward across piston 180'. Thus, the size of channels 198' may be controlled to control the speed of fluid flow and mixing across piston 180'. Piston 180' may also include channels on its outer surface, similar to slots 182 on piston 180 of FIG. 10, to further direct fluid flow. Piston 180' may only need to travel a short distance before the seal is broken, which allows for minimal head space above piston 180'. The broken seal leads to a gas-generating chemical reaction inside actuator assembly 120' of the second exemplary delivery device, as discussed above with respect to device 100.

5. Third Delivery Device

Figure 32:
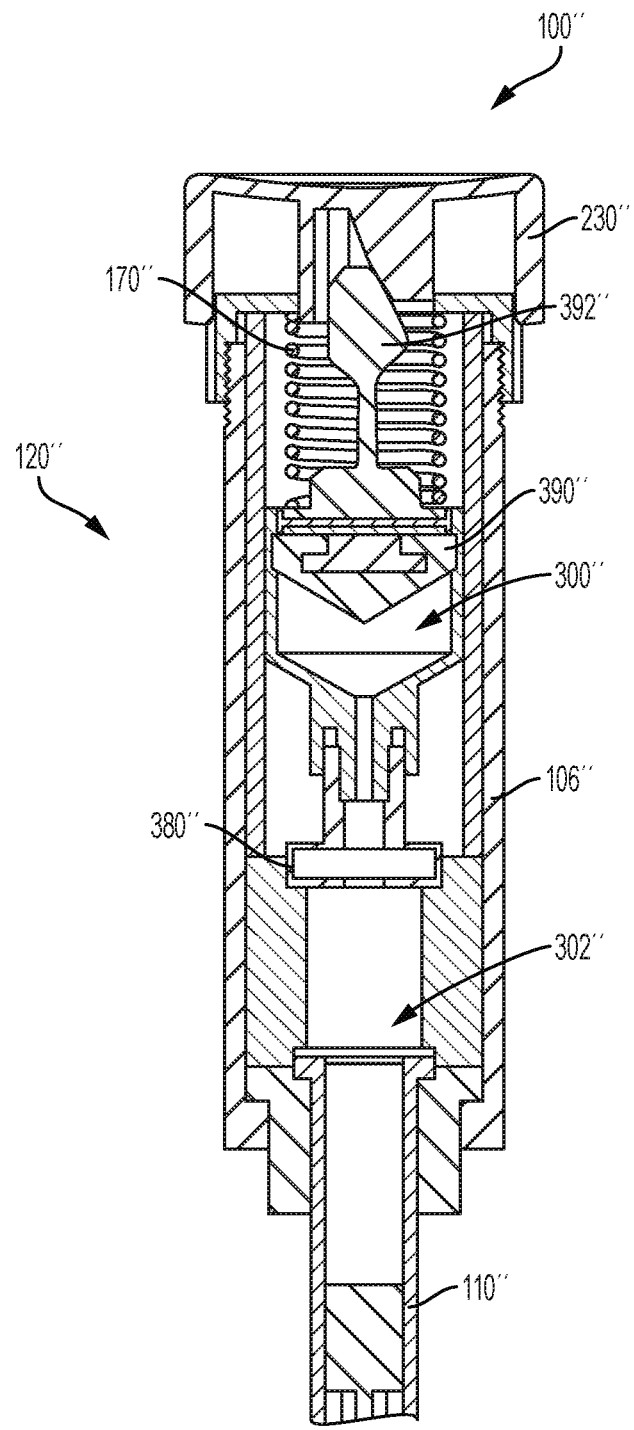
FIG. 32 is a cross-sectional view of a third exemplary actuator assembly of the present disclosure.

FIG. 32 shows a third exemplary delivery device 100" of the present disclosure. The device 100" is similar to device 100, with like reference numerals indicating like parts, except as described below. Device 100" may include a syringe 110", an auto-injector pen, or another suitable delivery device. The following components of actuator assembly 120" are shown in FIG. 32: a barrel 106" having an actuation chamber 300" and a reaction chamber 302", a one-way valve 380" (e.g., a check valve, an umbrella valve), a plunger 390" having a stem 392", a spring 170", and a button 230". Actuator assembly 120" may include additional components not shown in the drawings, such as a lower plug (similar to lower plug 140 of device 100) or a lower cap (similar to lower cap 240 of device 100).

Device 100" may have a loaded and locked configuration in which the one-way valve 380" separates a first reagent (e.g., aqueous citric acid) in actuation chamber 300" from a second reagent (e.g., potassium bicarbonate) in reaction chamber 302". Button 230" may be biased upward relative to barrel 106" under the force of spring 170". Button 230" may also be prevented from moving downward relative to barrel 106" due to a physical interference with stem 392" of plunger 390".

When device 100" is ready for use, device 100" may be moved from the locked configuration to an unlocked configuration. This step may involve rotating button 230" relative to stem 392" to eliminate the prior interference with stem 392". In this unlocked configuration, button 230" may be free to move downward relative to barrel 106", as shown in FIG. 32.

From the locked configuration, device 100" may be moved to a delivery configuration. This step may involve pressing button 230" downward relative to barrel 106". Initially, stem 392" may frictionally engage barrel 106" such that the downward movement of button 230" compresses spring 170". When the energy stored in the compressed spring 170" is sufficient to overcome the frictional engagement between stem 392" and barrel 106", spring 170" may release and drive plunger 390" downward relative to barrel 106". Advantageously, spring 170" may promote fast and consistent movement of plunger 390".

The downward movement of plunger 390" forces the first reagent out of actuation chamber 300". Because spring 170" may promote fast and consistent movement of plunger 390", spring 170" may also promote fast and consistent delivery of the first reagent. The first reagent may travel across one-way valve 380" and into reaction chamber 302" to mix with the second reagent already present in reaction chamber 302". This mixing leads to a gas-generating chemical reaction inside reaction chamber 302", as discussed above with respect to device 100. The pressure inside reaction chamber 302" may close one-way valve 380", thereby preventing the generated gas and other materials from escaping upward (i.e., back-flowing) into actuation chamber 300".

6. Liquid Absorption

As discussed above with respect to device 100, a liquid reagent may be stored in actuation chamber 300 in the pre-delivery or loaded configuration (FIG. 33) and travel into reaction chamber 302 in the delivery configuration (FIG. 34), where the liquid reagent mixes and reacts with a dry reagent. The liquid present in reaction chamber 302 in the delivery configuration (FIG. 34) may be a mixture of any unreacted liquid reagent from actuation chamber 300 and/or any liquids produced during the chemical reaction in reaction chamber 302. The mixture may also contain dissolved solids, such as the dry reagent and/or any solids produced during the chemical reaction in reaction chamber 302. In certain embodiments, the mixture may contain water and, as such, may be considered an aqueous mixture.

Figure 34:
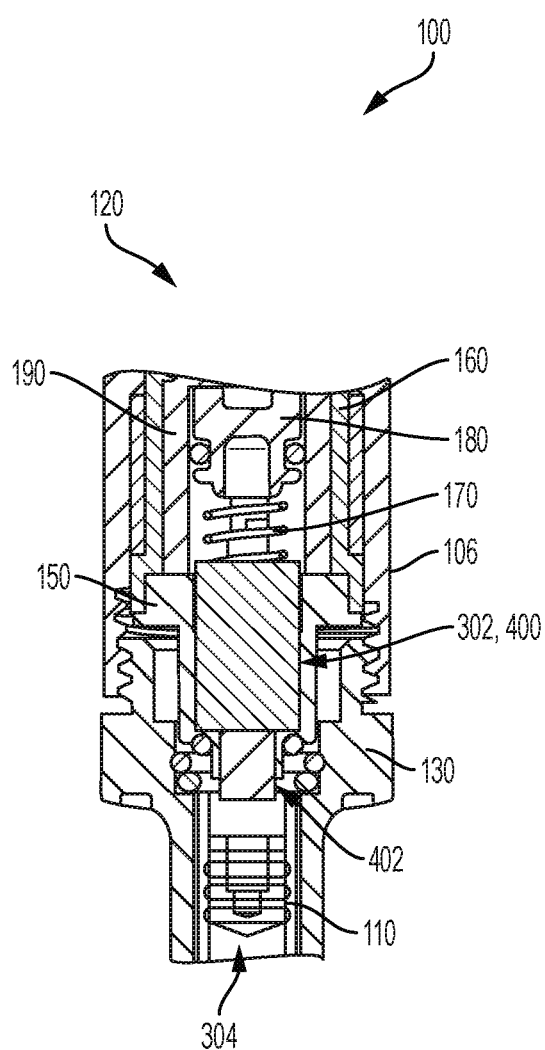
FIG. 34 is a cross-sectional view of the first device of FIG. 1 in the delivery configuration, the actuator assembly also including the absorbent powder and the filter.

Device 100 or any of the other devices described above may include one or more liquid absorbents (not shown) to absorb excess liquid from the mixture present in reaction chamber 302 in the delivery configuration (FIG. 34). In certain embodiments, the absorbent(s) may absorb a majority of the liquid present in reaction chamber 302 in the delivery configuration (FIG. 34). Based on the proportion, location, and properties of the absorbent(s) in reaction chamber 302, the absorption may be controlled to avoid interfering with (e.g., slowing) the chemical reaction in reaction chamber 302 while preventing liquid from entering therapeutic fluid chamber 304.

A first exemplary absorbent is an absorbent powder 400 (FIGS. 33 and 34), such as a super absorbent polymer (SAP) powder (e.g., hydrogel). The absorbent powder 400 may be chosen based on its absorption rate and capacity, long-term stability, price, chemical compatibility with reactants and device materials, liquid retention under pressure, and chemical safety. The absorption rate may be controlled by varying the particle size of the absorbent powder 400. For example, the particle size range of absorbent powder 400 may be 150 microns or less, 250 microns or less, or other suitable ranges. An exemplary absorbent powder 400 is poly(acrylic acid) sodium salt (i.e., sodium polyacrylate) with light cross-linking or other suitable salt of poly(acrylic acid) such as poly(acrylic acid) potassium salt (i.e., potassium polyacrylate) with light cross-linking. The absorption characteristics of the salt may correspond to the amount of cross-linking.

Figure 33:
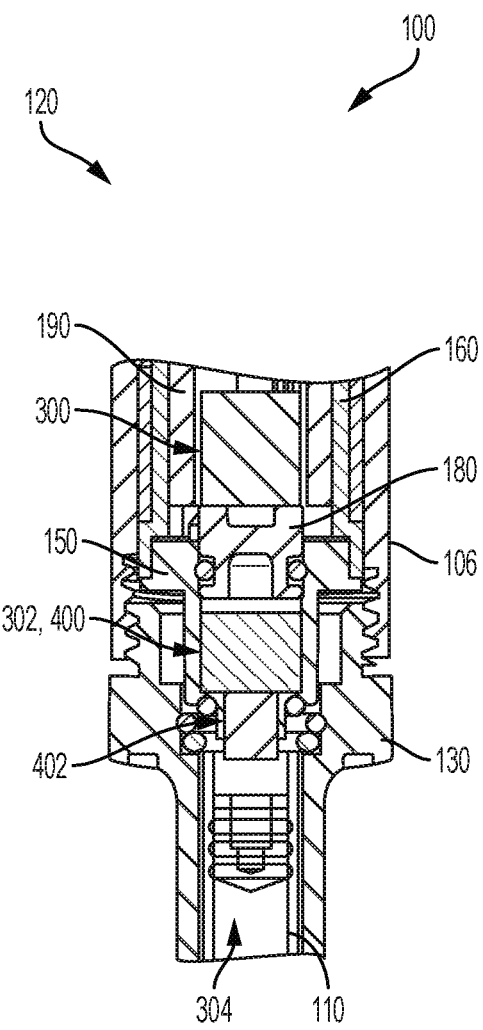
FIG. 33 is a cross-sectional view of the first device of FIG. 1 in the locked and loaded configuration, the actuator assembly also including an absorbent powder and a filter.

In the initial, loaded configuration, absorbent powder 400 may be mixed with the dry reagent. As shown in FIG. 33, absorbent powder 400 is mixed with the second reagent (e.g., potassium bicarbonate) in reaction chamber 302.

In the delivery configuration, when the liquid reagent mixes and reacts with the dry reagent, absorbent powder 400 may absorb excess liquid from the liquid mixture and swell. As shown in FIG. 34, absorbent powder 400 may absorb excess liquid from the liquid mixture in reaction chamber 302 after the first reagent (e.g., aqueous citric acid) leaves actuation chamber 300 to mix and react with the second reagent in reaction chamber 302. For example, absorbent powder 400 may absorb excess liquid reagent and/or liquid product present in reaction chamber 302.

A viscosity modifier polymer may be provided in addition to or alternatively to the absorbent powder 400 to dissolve in and thereby increase the viscosity of the aqueous reaction mixture. Exemplary viscosity modifiers include poly(ethylene oxide), xanthan gum, and poly(ethylene glycol) methyl ether, for example. Such materials (e.g., powders) may modify the viscosity of the aqueous mixture in reaction chamber 302 through dissolution such that the liquid becomes too viscous to flow into therapeutic fluid chamber 304.

A second exemplary absorbent is a gas-permeable, hydrophilic filter 402. Filter 402 may be placed substantially between reaction chamber 302 and therapeutic fluid chamber 304 (i.e., downstream of reaction chamber 302 and upstream of therapeutic fluid chamber 304). In the initial, loaded configuration, as shown in FIG. 33, filter 402 may help contain the second reagent (e.g., potassium bicarbonate) in reaction chamber 302. In the delivery configuration, as shown in FIG. 34, filter 402 may absorb any liquids that try to enter therapeutic fluid chamber 304. For example, filter 402 may absorb any liquid reagent and/or liquid product that try to enter therapeutic fluid chamber 304. Filter 402 may also block any solids or particles that try to enter therapeutic fluid chamber 304. Filter 402 is adapted to allow the passage of the produced gas in reaction chamber 302 toward plunger 116 of syringe 110 to deliver therapeutic fluid from therapeutic fluid chamber 304, as discussed above. An exemplary filter 402 is formed from virgin cotton having randomly oriented fibers. In one embodiment, the cotton is rolled into a cylinder shape or other suitable shape and press fit into the outlet of reaction chamber 302 during assembly. Other exemplary filters 402 are formed from natural fibers, sponges, cellulose (e.g., bonded cellulose acetate), absorbent cloth (e.g., ShamWOW® cloths), and foams. If necessary, a housing (not shown) may be provided to hold filter 402 in place. The housing may include a molded plug that is friction fit in the outlet of reaction chamber 302, similar to shaft 142 of lower plug 140 (FIG. 5) of device 100. In one embodiment, lower cap 240 (FIG. 25) is coupled over the outlet containing filter 402 for storage prior to attaching actuator assembly 120 to a syringe 110 or other delivery device.

Absorbent powder 400 (and/or the viscosity modifier powder) and filter 402 may be used alone or in combination. It is also within the scope of the present disclosure to physically combine absorbent powder 400 with filter 402, such as by distributing absorbent powder 400 throughout filter 402 or by placing absorbent powder 400 within a recess of filter 402. In one embodiment, absorbent powder 400 (and/or the viscosity modifier) is provided both in filter 402 and with the second reagent in reaction chamber 302.

Device 100, device 100', and/or device 100" may have other features disclosed in U.S. Pat. No. 9,321,581 titled "Process and Device for Delivery of Fluid by Chemical Reaction," the disclosure of which is expressly incorporated herein by reference in its entirety.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A device for delivering a therapeutic fluid by chemical reaction, the device comprising:
   a barrel having a first chamber, a second chamber, and a third chamber;
   a piston positioned between the first and second chambers of the barrel;
   a spring configured to move the piston;
   a plunger positioned between the second and third chambers of the barrel; and
   an actuator having:
      a locked configuration in which the actuator is prevented from moving axially relative to the barrel;
      an unlocked configuration in which the actuator is capable of moving axially relative to the barrel; and
      a delivery configuration in which the actuator moves axially relative to the barrel;

wherein:
in the locked and unlocked configurations, the first chamber contains a first reagent, the second chamber contains a second reagent and is separated from the first chamber by the piston, and the third chamber contains the therapeutic fluid; and in the delivery configuration, the spring moves the piston to place the first chamber in communication with the second chamber such that the first and second reagents react to generate a gas that drives the plunger to deliver the therapeutic fluid from the third chamber, the device further comprising a C-shaped ring that holds the actuator downward relative to the barrel in the delivery configuration to prevent the actuator from returning upward to the unlocked configuration.

2. The device of claim 1, further comprising a plug coupled to the barrel between the piston and the plunger, wherein the plug seals the second chamber in the locked and unlocked configurations and opens the second chamber in the delivery configuration.

3. The device of claim 1, further comprising at least one absorbent configured to absorb liquid in the second chamber before the liquid reaches the third chamber.

4. The device of claim 3, wherein the at least one absorbent is a super absorbent polymer.

5. The device of claim 4, wherein the super absorbent polymer is mixed with the second reagent in the second chamber.

6. The device of claim 3, wherein the at least one absorbent is a gas-permeable filter positioned upstream of the third chamber.

7. The device of claim 1, wherein the
actuator is configured to rotate relative to the barrel between the locked configuration and the unlocked configuration.

8. The device of claim 1, wherein the piston includes at least one locking tab that extends radially outward and the actuator includes at least one locking tab that extends radially inward, wherein the at least one locking tab of the piston is aligned beneath the at least one locking tab of the actuator in the locked configuration and is offset from the at least one locking tab of the actuator in the unlocked configuration.

9. The device of claim 8, wherein the at least one locking tab of the actuator includes a plurality of locking tabs, and the actuator includes a plurality of channels between the plurality of locking tabs, wherein in the unlocked configuration, the piston travels upward through the plurality of channels and the first reagent travels downward through the plurality of channels.

10. The device of claim 8, wherein the at least one locking tab of the actuator includes a plurality of locking tabs, and the actuator further includes a plurality of channels between the plurality of locking tabs, wherein in the unlocked configuration, the piston travels upward through the plurality of channels and the first reagent travels around the piston.

11. The device of claim 1, wherein the barrel includes a lock indicator window and the actuator includes a lock indicator tab visible to a user through the lock indicator window, wherein the lock indicator tab translates through the lock indicator window from a first position in the locked configuration to a second position in the unlocked configuration.

12. The device of claim 11, wherein the lock indicator tab snaps into the lock indicator window to retain the actuator in the barrel.

13. The device of claim 1, wherein the piston travels axially upward and toward the actuator in the unlocked configuration.

14. A device for delivering a therapeutic fluid by chemical reaction, the device comprising:
a barrel having a first chamber containing a first reagent, a second chamber containing a second reagent and an absorbent powder, and a third chamber containing the therapeutic fluid;
a piston positioned between the first and second chambers of the barrel;
a plunger positioned between the second and third chambers of the barrel; and
an actuator configured to move the piston to place the first chamber in communication with the second chamber such that the first and second reagents react to form a liquid mixture and a gas, wherein at least a portion of the liquid mixture is absorbed by the absorbent powder, and wherein the gas drives the plunger to deliver the therapeutic fluid from the third chamber.

15. The device of claim 14, wherein the first reagent is a liquid and the second reagent is a solid.

16. The device of claim 14, wherein the second reagent is mixed with the absorbent powder.

17. The device of claim 14, wherein the liquid mixture includes at least one liquid product from the reaction between the first and second reagents.

18. The device of claim 17, wherein the liquid mixture includes an unreacted portion of the first reagent.

19. The device of claim 14, wherein the actuator moves in a first longitudinal direction relative to the barrel to actuate the device, and the piston moves in a second longitudinal direction opposite the first longitudinal direction to place the first chamber in communication with the second chamber.

20. The device of claim 14, wherein the actuator comprises:
a shuttle received in the barrel, and
a button coupled to the barrel and actuatable by a user, wherein the shuttle includes a keyway and the barrel includes a key that extends radially inward to interact with the keyway of the shuttle.

21. The device of claim 14, wherein the barrel comprises:
an upper housing;
an adapter coupled to the upper housing and having an inner shoulder; and
a syringe having an upper rim configured to rest upon the inner shoulder of the adapter.

22. The device of claim 14, wherein the absorbent powder is a super absorbent polymer.

23. The device of claim 14, further including a gas-permeable filter positioned upstream of the third chamber.

* * * * *